(12) United States Patent
Lang et al.

(10) Patent No.: US 11,497,812 B2
(45) Date of Patent: *Nov. 15, 2022

(54) COMPOSITIONS AND METHODS FOR INHIBITING THE ACTIVITY OF LAR FAMILY PHOSPHATASES

(71) Applicant: CASE WESTERN RESERVE UNIVERSITY, Cleveland, OH (US)

(72) Inventors: Bradley T. Lang, Cleveland, OH (US); Jared M. Cregg, Cleveland, OH (US); Jerry Silver, Bay Village, OH (US); Yi-Lan Weng, Baltimore, MD (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/983,879

(22) Filed: Aug. 3, 2020

(65) Prior Publication Data

US 2021/0205460 A1    Jul. 8, 2021

Related U.S. Application Data

(63) Continuation of application No. 15/949,967, filed on Apr. 10, 2018, now Pat. No. 10,729,777, which is a continuation-in-part of application No. 14/391,589, filed as application No. PCT/US2013/035831 on Apr. 9, 2013, now Pat. No. 9,937,242.

(60) Provisional application No. 61/621,623, filed on Apr. 9, 2012.

(51) Int. Cl.
| | |
|---|---|
| *A61K 47/42* | (2017.01) |
| *A61P 25/16* | (2006.01) |
| *A61P 25/28* | (2006.01) |
| *A61K 9/00* | (2006.01) |
| *A61K 38/16* | (2006.01) |
| *A61K 47/64* | (2017.01) |
| *A61K 38/17* | (2006.01) |

(52) U.S. Cl.
CPC ............ *A61K 47/42* (2013.01); *A61K 9/0019* (2013.01); *A61K 38/162* (2013.01); *A61K 38/179* (2013.01); *A61K 47/645* (2017.08); *A61P 25/16* (2018.01); *A61P 25/28* (2018.01); *A61K 2121/00* (2013.01)

(58) Field of Classification Search
None
See application file for complete search history.

(56) References Cited

U.S. PATENT DOCUMENTS

| | | | |
|---|---|---|---|
| 5,804,604 A | 9/1998 | Frankel et al. | |
| 6,841,535 B2 | 1/2005 | Divita et al. | |
| 8,148,541 B2 | 4/2012 | Ryu et al. | |
| 9,744,188 B2 | 8/2017 | Flanagan et al. | |
| 9,937,242 B2 * | 4/2018 | Lang | ............... C12Y 301/03048 |
| 10,206,967 B2 * | 2/2019 | Lang | ...................... C07K 14/00 |
| 10,258,672 B2 * | 4/2019 | Silver | .................. A61K 38/005 |
| 10,729,777 B2 * | 8/2020 | Lang | ..................... A61K 47/645 |
| 10,786,541 B2 * | 9/2020 | Lang | ...................... C07K 14/00 |
| 10,898,550 B2 * | 1/2021 | Silver | .................. A61K 38/465 |
| 2004/0138255 A1 | 7/2004 | Huang et al. | |
| 2009/0202544 A1 | 8/2009 | Suciu-Foca et al. | |
| 2012/0045459 A1 | 2/2012 | Mackeigan et al. | |
| 2012/0231014 A1 | 8/2012 | Flanagan et al. | |
| 2015/0084328 A1 | 3/2015 | Kampfe et al. | |

FOREIGN PATENT DOCUMENTS

| | | | |
|---|---|---|---|
| EP | 0028742 | A1 | 5/1981 |
| EP | 0376839 | A1 | 7/1990 |
| FR | 2124846 | A5 | 9/1972 |
| JP | H09504689 | A | 5/1997 |
| JP | 2010524847 | A | 7/2010 |
| JP | 2012530105 | A | 11/2012 |
| JP | 2015510941 | A | 4/2015 |
| JP | 2015516391 | A | 6/2015 |
| WO | 2002083182 | A2 | 10/2002 |
| WO | 2009072726 | A1 | 6/2009 |
| WO | 2010/129681 | A1 | 11/2010 |
| WO | 2011022462 | A2 | 2/2011 |
| WO | 2012/0019086 | A2 | 2/2012 |
| WO | 2012/019086 | A2 | 2/2012 |
| WO | 2013/155103 | A1 | 10/2013 |

OTHER PUBLICATIONS

Applicant Case Western Reserve University; "Compositions and Methods for Treating Alzheimer's Desease"; European Patent Application No. EP18813399; EESR; dated Mar. 8, 2021; 9 pgs.

F. Jeppsson, et al.; "Discovery of AZD3839, a Potent and Selective BACE1 Inhibitor Clinical Candidate for the Treatment of Alzheimer Disease", Journal of Biological Chemistry, vol. 287, No. 49, Nov. 30, 2012, p. 41245-41257, XP055299016, ISSN: 0021-9258, DOI: 10.1074/jbc.M112.409110.

Gu, et al.; "Alzheimer's disease pathogenesis is dependent on neuronal receptor ???s"; bioRxiv; 58 pp.; Retrieved Apr. 22, 2021, 2016; doi: https://doi.org/10.1101/079806.

(Continued)

*Primary Examiner* — Christina Bradley

(74) *Attorney, Agent, or Firm* — Tarolli, Sundheim, Covell & Tummino LLP

(57) ABSTRACT

A method of inhibiting and/or reducing the activity, signaling, and/or function of leukocyte-common antigen related (LAR) family of phosphatases in a cell of a subject induced by proteoglycans includes administering to the cell a therapeutic agent that inhibits one or more of catalytic activity, signaling, and function of the LAR family phosphatases without inhibiting binding to or activation the LAR family phosphatases by the proteoglycans.

20 Claims, 9 Drawing Sheets

Specification includes a Sequence Listing.

(56) References Cited

OTHER PUBLICATIONS

Japanese Office Action; Japanese Application No. 2019-565526; dated Apr. 23, 2021; 5 pgs.
Melanie J. Chagnon, et al.; "Functional Significance of the LAR Receptor Protein Tyrosine Phosphatase Family in Development and Diseases"; Biochemistry and Cell Biology. Biochimie Et Biologie Cellulaire; vol. 82, No. 6; Dec. 1, 2004; pp. 664-675, XP055769264, CA; ISSN: 0829-8211, DOI: 10.1139/P04-120.
Melnikova Tatiana, et al.; G-Secretase Modulator Enhances the AB-Lowering Effect of BACE1 Inhibitor in Mouse Models of Alzheimer's Disease, Alzheimer's & Dementia: The Journal of the Alzheimer's Association, vol. 12, No. 7, Oct. 1, 2016, XP029763344, ISSN: 1552-5260, DOI: 10.1016/J. JALZ.2016.06.719.
Russo, Alberto, et al.; "Pharmacokinetic/Pharmacodynamic Modeling of CSF AB1-40 Reduction in an Early Alzheimer's Disease Study of JNJ-54861911, an Oral Bace1 Inhibitor", Alzheimer's & Dementia: The Journal of the Alzheimer's Association, vol. 12, No. 7, Jan. 1, 2016, XPO029769823, ISSN: 1552-5260, DOI: 10.1016/J. JALZ.2016.06.1215.
Aricescu, A. Radu, et al., "Heparan Sulfate Proteoglycans Are Ligands for Receptor Protein Tyrosine Phosphatase o", Molecular and Cellular Biology, Mar. 2002, p. 1881-1892, vol. 22, No. 6.
Brown, Joshua M., et al., "A sulfated carbohydrate epitope inhibits axon regeneration after injury", PNAS, Mar. 27, 2012, vol. 109, No. 13, pp. 4768-4773.
Carey, D.M., et al., "Association of Cell Surface Heparan Sulfate Proteoglycans of Schwann Cells with Extracellular Matrix Proteins", J. Biol. Chem, 1990, 265L20627-20633.
Coles, Charlotte, et al. Proteoglycan-Specific Molecular Switch for RPTPcr Clustering and Neuronal Extension, Science. Apr. 22, 2011, 332(6028): 484-488.
Cortes, Mauricio, et al., "Sulfation if Chondroitin Sulfate Proteoglycans is necessary for proper Indian hedgehot signaling in the developing growth plate", Development 136, 1697-1706 (2009).
Dickendesher, Travis, L., "NgR1 and NgR3 are Receptors for Chondroitin Sulfate Proteoglycans", Nat. Neurosci.; 15(5): 703-712.
Examiner's Report for Canadian for Application No. 2,870,155, dated Nov. 27, 2018.
Extended European Search Report dated Oct. 30, 2015.
Fassler & Cooper, "BLAST Glossary," created Jul. 14, 2011, pp. 1-9, downloaded on Mar. 18, 2017 from www.ncbi.nim.nih.gov/books/NBK62051/.
Fisher Daniel, et al., "LAR is a functional receptor for CSPG Axon Growth Inhibitors", J. Neurosci. Oct. 5, 2011; 31 (40): 14051-14066.
Horn, Kevin, et al., "Another barrier to regeneration in the CNS: Activated macrophages induce extensive retraction of dystrophic axons through direct physical interactions", J. Neurosci. Sep. 17, 2008; 28(38):9330-9341.
Koren, et al., "Inhibition of the protein tyrosine phosphatase PTP1B: Potential therapy for obesity, insulin resistance and type-2 diabetes mellitus", Best Practice and Research Clinical Endocrinology and Metabolism, vol. 21, No. 4, pp. 621-640, Dec. 31, 2007.
Majeti, Ravindra, et al., "Dimerization-Induced Inhibition of Receptor Protein Tyrosine Phosphatase Function Through an Inhibitory Wedge", Science vol. 279, Jan. 2, 1998.
Office Action for Japanese Patent Application No. 2015-505856, dated Jan. 5, 2017.
Office action for Japanese Patent Application No. 2015-505856, dated Oct. 3, 2017.
Shen, Yingjie, et al., "PTPo is a Receptor for Chondroitin Sulfate Proteoglycan, an Inhibitor of Neural Regeneration", Science. Oct. 23, 2009; 326(5952: 592-596).
Tom, Veronica J., et al., "Studies in the Development and Behavior of the Dystrophic Growth Cone, the Hallark of Regeneration Failure, and an In Vitro Model of the Glial Scar and after Spinal Injury", The journal of Neuroscience, Jul. 21, 2004, 24 (29):6531-6539.
Xie, Youmei, et al., "Protein-Tyrosine Phosphatase (PTP) Wedge Domain Peptides: A Novel Approach for Inhibition of PTP Function and Augmentation of Protein-Tyrosine Kinase Function", J. Biol. Chem. 2006, 281-16482-16492.
Zipes "Influence of Myocardial Ischemia and Infarction on Autonomic Innervation of Heart," Circulation. 1990;82-1095-1105 (Year: 1990).
Applicant: Case Western Reserve University; "Compositions and Methods for Treating Myelin Disorders"; European Patent Application No. 18832119.4; Extended European Search Report; dated May 26, 2021; 10 pgs.
Japanese Application No. 2020-133525; Japanese Office Action dated Aug. 10, 2021; 2 pgs.
Li Heng et al; "Enhanced Regeneration and Functional Recovery After Spinal Root Avulsion by Manipulation of the Proteoglycan Receptor PTP [sigma]"; Scientific Reports, vol. 5, No. 1, Oct. 14, 2015; XP055778445, DOI: 10.1038/srep14923 Retrieved from the Internet: URL:HTTP://www.nature.com/articles/srep14923.
Motavaf Mahsa, et al; "Attempts to Overcome Remyelination Failure: Toward Opening New Therapeutic Avenues for Multiple Sclerosis"; Cellular and Molecular Neurobiology, Springer New York, US, vol. 37, No. 8, Feb. 21, 2019, pp. 1335-1348, XPO36333800, ISSN: 0272-4340, DOI: 10.1007/S10571-017-0472-6.
Japanese Application No. 2020-133525; Japanese office Action dated Mar. 22, 2022; 6 pgs.
Jiang, Guoqiang, et al. "Dimerization inhibits the activity of receptor-like protein-tyrosine phosphatase-a." Nature 401.6753 (1999): 606-610.
Applicant: Case Western Reserve University; "Methods and Compositions for Inducing Neural Plasticity"; European Application No. EP19857885; Extended European Search Report; dated May 11, 2022; 7 pgs.

\* cited by examiner

**Adult Sensory DRG Neurons
5 day exposure to gradient**

Gradients of CSPG induce Stabilization

92% of growth cones (22/24) were immotile at 4-6 days in vitro

ISP Relieves Proteoglycan Inhibition *in vitro*

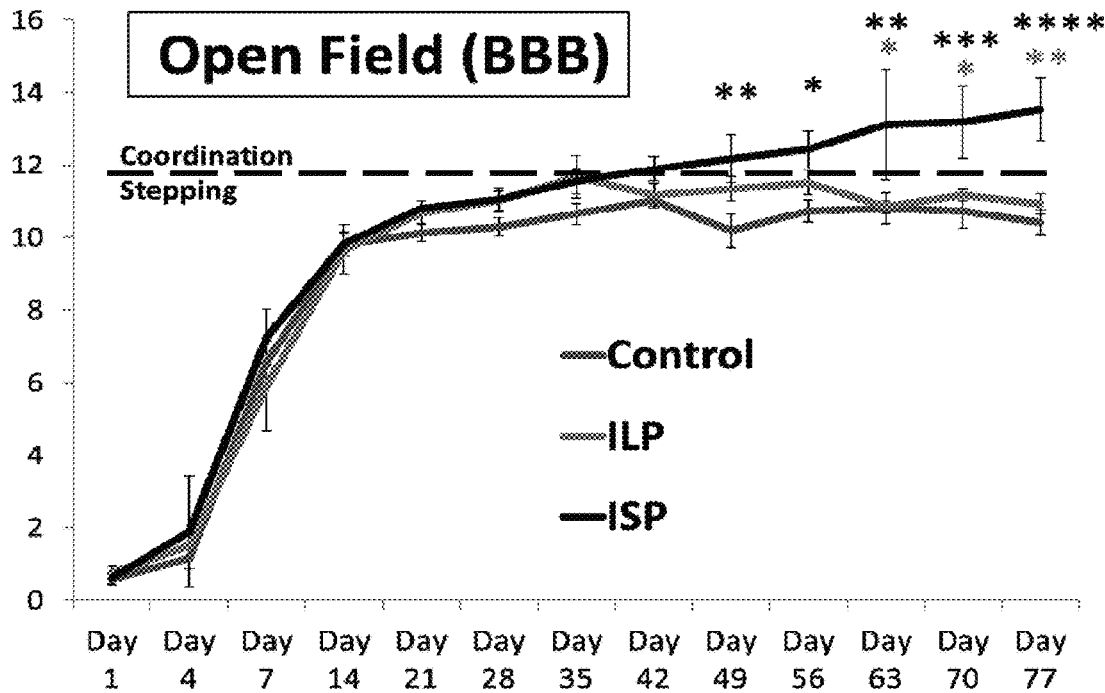

- BBB is the standard locomotor recovery scale following SCI
  - 0= Complete Paraplegia
  - 21= Normal Locomotion
  - 12, 13, 14= Occasional, frequent, and Consistent hindlimb/forelimb coordination, respectively
- Animals reached a maximum score of 19
  - Consistent coordination, consistent toe clearance, tail held consistently high and toe placement is parallel on initial contact and liftoff

Fig. 8

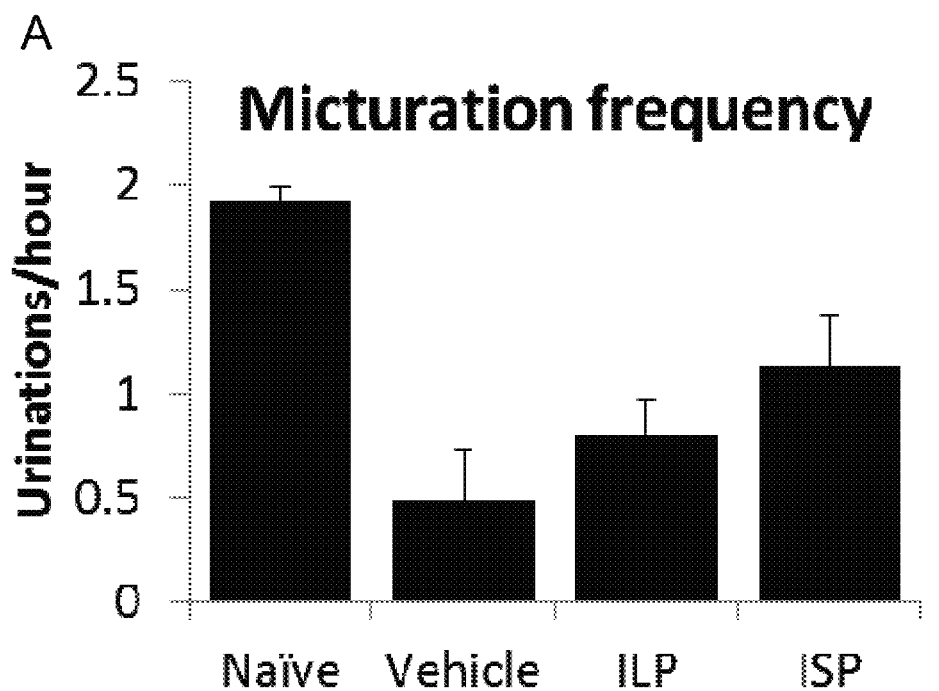
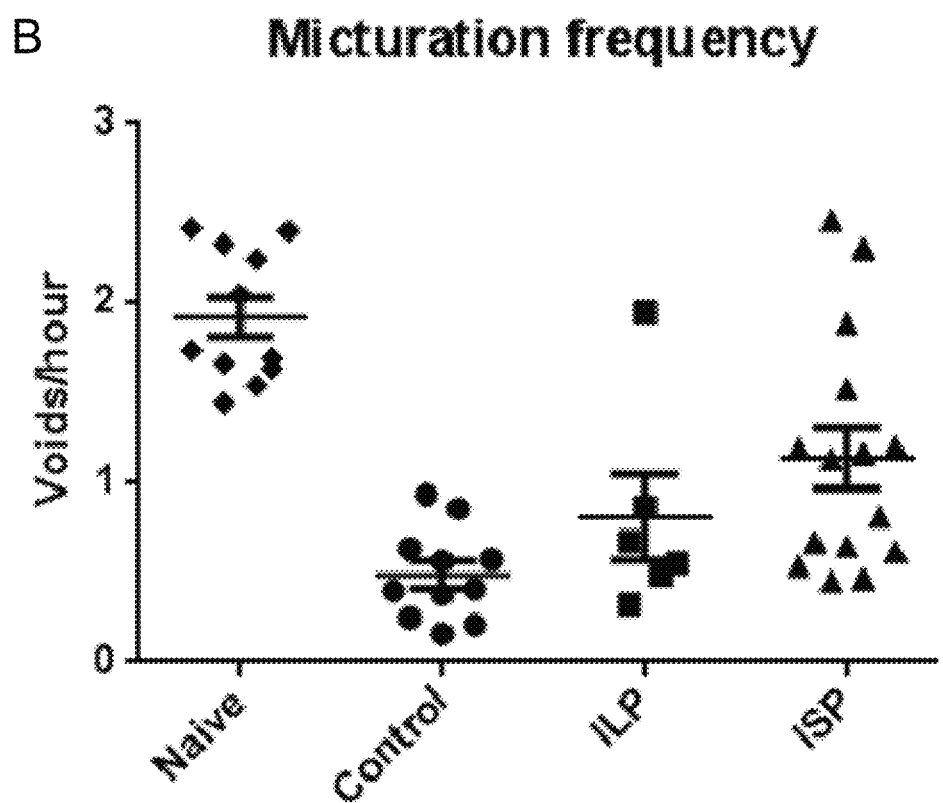
Figs. 13A-B

COMPOSITIONS AND METHODS FOR INHIBITING THE ACTIVITY OF LAR FAMILY PHOSPHATASES

RELATED APPLICATION

This application is a Continuation-in-Part of U.S. patent application Ser. No. 14/391,589, filed Oct. 9, 2014, now U.S. Pat. No. 9,937,242, which is a National Phase Filing of PCT/US2013/035831, filed Apr. 9, 2013, which claims priority from U.S. Provisional Application No. 61/621,623, filed Apr. 9, 2012, the subject matter of which are incorporated herein by reference in their entirety.

GOVERNMENT FUNDING

This invention was made with government support under Grant No. NS025713 awarded by The National Institutes of Health (NIH). The United States government has certain rights in the invention.

TECHNICAL FIELD

This application relates to compositions and methods for inhibiting or reducing the activity, signaling, and/or function of leukocyte-common antigen related (LAR) family of phosphatases and to methods and compositions for treating diseases, disorders, and/or conditions associated with activity, signaling, and/or function of LAR family phosphatases.

BACKGROUND

Spinal cord injury and other central nervous system (CNS) injuries can cause permanent disability or loss of movement (paralysis) and sensation below the site of the injury. Recovery after CNS injury is minimal, leading to substantial current interest in potential strategies to overcome this challenge. A fundamental obstacle facing efforts to improve neuronal function after injury is the inability of the adult CNS to regenerate.

Two well-known classes of regeneration inhibitors are myelin-associated inhibitors (MAG, Nogo and OMGP); and inhibitors in scar tissue formed by glia at the injury site (e.g., chondroitin sulfate proteoglycan (CSPG)). CSPG is involved not only in traumatic injury, but also many other CNS diseases including neurodegeneration. Example receptors for myelin-associated inhibitors include Pir B and NgR.

CSPG present a barrier to axon regeneration, yet no specific receptor for the inhibitory effect of CSPG has been identified previously. More specifically, CSPG shows dramatic upregulation after neural injury, both within the extracellular matrix of scar tissue and in the perineuronal net within more distant targets of the severed axons. The inhibitory nature of CSPG is not only reflected in the formation of dystrophic axonal retraction bulbs that fail to regenerate through the lesion, but also in the limited ability for collateral sprouting of spared fibers. Although it has been known for nearly two decades that sulfated proteoglycans are major contributors to the repulsive nature of the glial scar, the precise inhibitory mechanism was poorly understood. Thus, there remains an urgent need for mechanisms that modulate CSPG function.

SUMMARY

Embodiments described herein relate to methods of inhibiting and/or reducing the activity, signaling, and/or function of leukocyte-common antigen related (LAR) family of phosphatases in a cell of a subject induced by proteoglycans. The methods include administering to the cell a therapeutic agent that inhibits one or more of catalytic activity, signaling, and function of the LAR family phosphatases without inhibiting binding to or activation the LAR family phosphatases by the proteoglycans.

In some embodiments, the LAR family phosphatase is a receptor protein tyrosine phosphatase sigma (PTPσ), and the therapeutic agent includes a therapeutic peptide having an amino acid sequence that is at least about 65%, at least about 70%, at least about 75%, at least about 80%, at least about 85%, at least about 90%, or at least about 95% homologous to about 10 to about 20 consecutive amino acids of the wedge domain of PTPσ. For example, therapeutic agent can include a therapeutic peptide selected from the group consisting of SEQ ID NOs: 9-33.

In other embodiments, the LAR family phosphatase is a receptor protein tyrosine phosphatase sigma (PTPσ), and the therapeutic agent can include a therapeutic peptide at least about 65%, at least about 70%, at least about 75%, at least about 80%, at least about 85%, at least about 90%, or at least about 95% homologous to the amino acid sequence of SEQ ID NO: 37. The therapeutic peptide can include, for example, a conservative substitution of an amino acid of at least one, two, three, or four of residue 4, 5, 6, 7, 9, 10, 12, or 13 of SEQ ID NO: 37.

In some embodiments, the cell is a neural cell, glial cell, glial progenitor cell, or a neural progenitor cell.

In other embodiments, the therapeutic agent includes a transport moiety that is linked to the therapeutic peptide and facilitates uptake of the therapeutic peptides by the cell. For example, the transport moiety can be an HIV Tat transport moiety.

In still other embodiments, the cell is in a subject being treated, and the therapeutic agent is administered locally or systemically to the subject being treated.

In yet other embodiments, the therapeutic peptide is expressed in the cell.

Embodiments herein also relate to methods of treating diseases, disorders, and/or conditions associated with activation and signaling of LAR family phosphatases. The methods include administering to a cell of the subject a therapeutic agent that inhibits one or more of catalytic activity, signaling, and function of the LAR family phosphatases without inhibiting binding to or activation the LAR family phosphatases by the proteoglycans.

In some embodiments, the disease, disorder, and/or condition includes at least one of a disease, disorder, and/or condition of the nervous system.

In other embodiments, the disease, disorder, and/or condition of the nervous system includes at least one of a neurological disorder, neuropsychiatric disorder, neural injury, neural toxicity disorder, a neuropathic pain, and neural degenerative disorders.

For example, the neurological disorder can include at least one of traumatic or toxic injuries to peripheral or cranial nerves, spinal cord or to the brain, cranial nerves, traumatic brain injury, stroke, cerebral aneurism, and spinal cord injury. The neurological disorder can also include at least one of Alzheimer's disease, dementias related to Alzheimer's disease, Parkinson's, Lewy diffuse body diseases, senile dementia, Huntington's disease, Gilles de la Tourette's syndrome, multiple sclerosis, amyotrophic lateral sclerosis, hereditary motor and sensory neuropathy, diabetic neuropathy, progressive supranuclear palsy, epilepsy, or Jakob-Creutzfieldt disease.

In some embodiments, the neural injury can be caused by or associated with at least one of epilepsy, cerebrovascular diseases, autoimmune diseases, sleep disorders, autonomic disorders, urinary bladder disorders, abnormal metabolic states, disorders of the muscular system, infectious and parasitic diseases neoplasms, endocrine diseases, nutritional and metabolic diseases, immunological diseases, diseases of the blood and blood-forming organs, mental disorders, diseases of the nervous system, diseases of the sense organs, diseases of the circulatory system, diseases of the respiratory system, diseases of the digestive system, diseases of the genitourinary system, diseases of the skin and subcutaneous tissue, diseases of the musculoskeletal system and connective tissue, congenital anomalies, or conditions originating in the perinatal period.

Still other embodiments described herein relate to a therapeutic agent for promoting at least one of neural cell growth, motility, survival and plasticity. The therapeutic agent includes a therapeutic peptide having an amino acid sequence that is at least about 65%, at least about 70%, at least about 75%, at least about 80%, at least about 85%, at least about 90%, or at least about 95% homologous to about 10 to about 20 consecutive amino acids of the wedge domain of PTPσ. For example, therapeutic agent can include a therapeutic peptide selected from the group consisting of SEQ ID NOs: 9-33.

In other embodiments, the therapeutic agent can include a therapeutic peptide at least about 65%, at least about 70%, at least about 75%, at least about 80%, at least about 85%, at least about 90%, or at least about 95% homologous to the amino acid sequence of SEQ ID NO: 37. The therapeutic peptide can include, for example, a conservative substitution of an amino acid of at least one, two, three, or four of residue 4, 5, 6, 7, 9, 10, 12, or 13 of SEQ ID NO: 37.

Yet other embodiments described herein relate to a pharmaceutical composition. The pharmaceutical composition includes a therapeutic agent that comprises a synthetic therapeutic peptide at least about 65%, at least about 70%, at least about 75%, at least about 80%, at least about 85%, at least about 90%, or at least about 95% homologous to SEQ ID NO: 37 and a transport moiety that is linked to the therapeutic peptide and facilitates uptake of the therapeutic peptides by a cell.

In some embodiments, the therapeutic peptide includes a conservative substitution of an amino acid of at least one of residue 4, 5, 6, 7, 9, 10, 12, or 13 of SEQ ID NO: 37.

In other embodiments, the therapeutic peptide includes an amino acid sequence selected from the group consisting of SEQ ID NOs: 9-33 and 37.

In still other embodiments, the therapeutic agent is a peptide having an amino acid sequence selected from the group consisting of SEQ ID NOs: 42-66 and 70.

BRIEF DESCRIPTION OF THE DRAWINGS

FIG. 8 illustrates a plots showing the Basso, Beattie and Bresnahan scored for post-spinal cord injury (SCI) locomotion of vehicle treated SCI animals and LAR peptide treated SCI animals at days 1 through day 77.

FIGS. 13(A-B) illustrate graphs showing micturition frequency of vehicle treated SCI animals and LAR peptide treated SCI animals.

DETAILED DESCRIPTION

Figure 1:
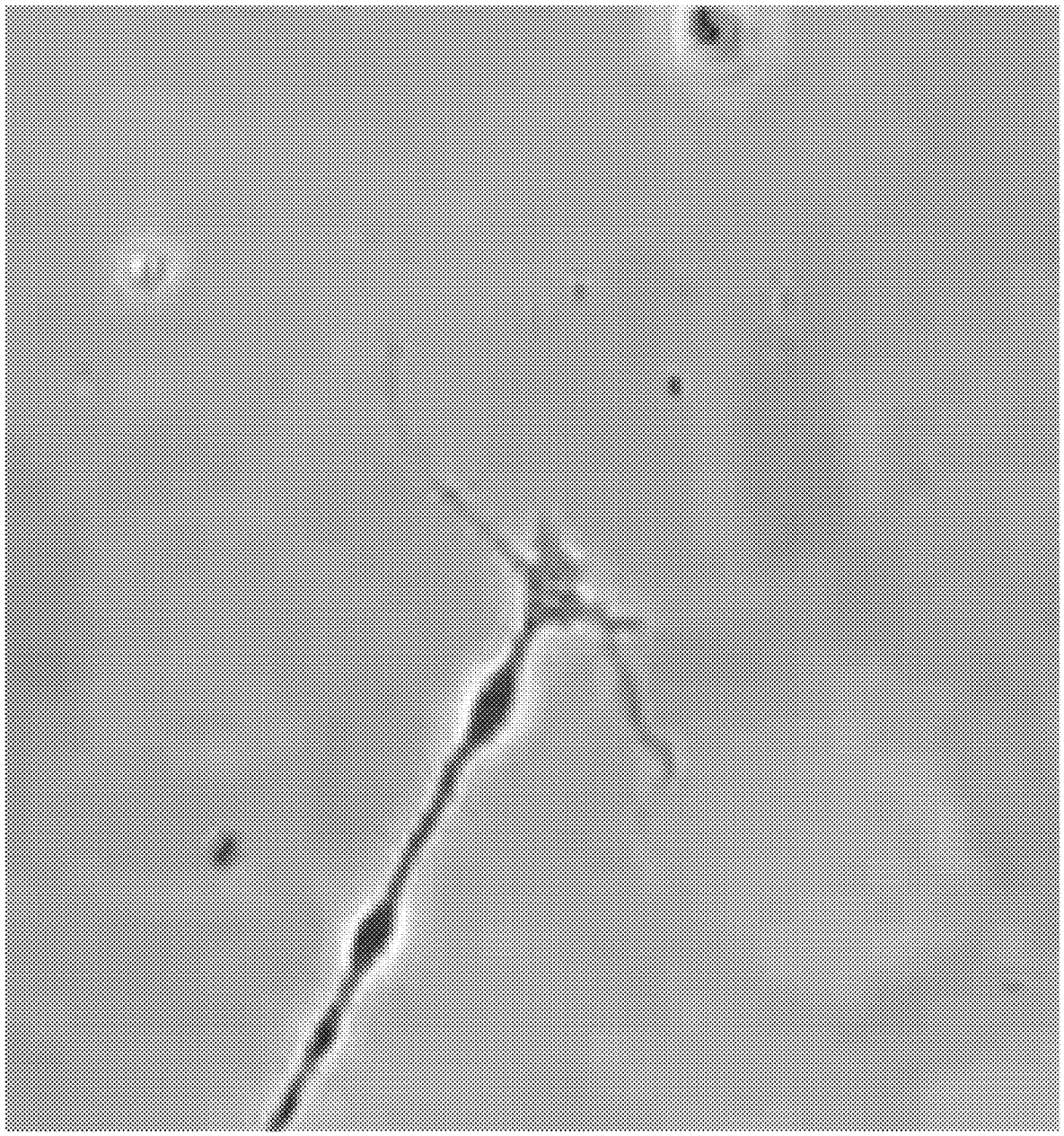
FIG. 1 illustrates a photograph of an adult sensory DRG neuron in a spot assay after 5 days exposure to a gradient of CSPG.

The embodiments described herein are not limited to the particular methodology, protocols, and reagents, etc., and as such may vary. The terminology used herein is for the purpose of describing particular embodiments only, and is not intended to limit the scope of the present invention, which is defined solely by the claims. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

As used herein, "one or more of a, b, and c" means a, b, c, ab, ac, bc, or abc. The use of "or" herein is the inclusive or.

As used herein, the term "administering" to a patient includes dispensing, delivering or applying an active compound in a pharmaceutical formulation to a subject by any suitable route for delivery of the active compound to the desired location in the subject (e.g., to thereby contact a desired cell such as a desired neuron), including administration into the cerebrospinal fluid or across the blood-brain barrier, delivery by either the parenteral or oral route, intramuscular injection, subcutaneous or intradermal injection, intravenous injection, buccal administration, transdermal delivery and administration by the rectal, colonic, vaginal, intranasal or respiratory tract route. The agents may, for example, be administered to a comatose, anesthetized or paralyzed subject via an intravenous injection or may be administered intravenously to a pregnant subject to stimulate axonal growth in a fetus. Specific routes of administration may include topical application (such as by eyedrops, creams or erodible formulations to be placed under the eyelid, intraocular injection into the aqueous or the vitreous humor, injection into the external layers of the eye, such as via subconjunctival injection or subtenon injection, parenteral administration or via oral routes.

As used herein, the term "antibody", includes human and animal mAbs, and preparations of polyclonal antibodies, synthetic antibodies, including recombinant antibodies (antisera), chimeric antibodies, including humanized antibodies, anti-idiotopic antibodies and derivatives thereof. A portion or fragment of an antibody refers to a region of an antibody that retains at least part of its ability (binding specificity and affinity) to bind to a specified epitope. The term "epitope" or "antigenic determinant" refers to a site on an antigen to which antibody paratope binds. Epitopes formed from contiguous amino acids are typically retained on exposure to denaturing solvents whereas epitopes formed by tertiary folding are typically lost on treatment with denaturing solvents. An epitope typically includes at least 3, at least 5, or 8 to 10, or about 13 to 15 amino acids in a unique spatial conformation. Methods of determining spatial conformation of epitopes include, for example, x-ray crystallography and 2-dimensional nuclear magnetic resonance. See, e.g., 66 EPITOPE MAPPING PROTOCOLS IN METS. IN MOLECULAR BIO. (Morris, ed., 1996); Burke et al., 170 J. Inf. Dis. 1110-19 (1994); Tigges et al., 156 J. Immunol. 3901-10).

As used herein, the term axonal "growth" or "outgrowth" (also referred to herein as "neuronal outgrowth") includes the process by which axons or dendrites extend from a neuron. The outgrowth can result in a new neuritic projection or in the extension of a previously existing cellular process. Axonal outgrowth may include linear extension of an axonal process by five cell-diameters or more. Neuronal growth processes, including neuritogenesis, can be evidenced by GAP-43 expression detected by methods such as immunostaining. "Stimulating axonal growth" means promoting axonal outgrowth.

As used herein the term, "central nervous system (CNS) neurons" include the neurons of the brain, the cranial nerves and the spinal cord.

As used herein, the term "dieback" refers to axonal retraction that occurs as a result of trauma to the axon.

As used herein, a "chimeric protein" or "fusion protein" is a fusion of a first amino acid sequence encoding a polypeptide with a second amino acid sequence defining a domain (e.g., polypeptide portion) foreign to and not substantially homologous with the domain of the first polypeptide. A chimeric protein may present a foreign domain, which is found (albeit in a different protein) in an organism, which also expresses the first protein, or it may be an "interspecies", "intergenic", etc. fusion of protein structures expressed by different kinds of organisms.

As used herein, the term "contacting neurons" or "treating neurons" refers to any mode of agent delivery or "administration," either to cells or to whole organisms, in which the agent is capable of exhibiting its pharmacological effect in neurons. "Contacting neurons" includes both in vivo and in vitro methods of bringing an agent of the invention into proximity with a neuron. Suitable modes of administration can be determined by those skilled in the art and such modes of administration may vary between agents. For example, when axonal growth of neurons is stimulated ex vivo, agents can be administered, for example, by transfection, lipofection, electroporation, viral vector infection, or by addition to growth medium.

As used herein, an "effective amount" of an agent or therapeutic peptide is an amount sufficient to achieve a desired therapeutic or pharmacological effect, such as an amount that is capable of activating the growth of neurons. An effective amount of an agent as defined herein may vary according to factors such as the disease state, age, and weight of the subject, and the ability of the agent to elicit a desired response in the subject. Dosage regimens may be adjusted to provide the optimum therapeutic response. An effective amount is also one in which any toxic or detrimental effects of the active compound are outweighed by the therapeutically beneficial effects.

As used herein, the term a "therapeutically effective amount" refers to an amount effective, at dosages and for periods of time necessary, to achieve the desired therapeutic result. A therapeutic result may be, e.g., lessening of symptoms, prolonged survival, improved mobility, and the like. A therapeutic result need not be a "cure."

As used herein, the term "expression" refers to the process by which nucleic acid is translated into peptides or is transcribed into RNA, which, for example, can be translated into peptides, polypeptides or proteins. If the nucleic acid is derived from genomic DNA, expression may, if an appropriate eukaryotic host cell or organism is selected, include splicing of the mRNA. For heterologous nucleic acid to be expressed in a host cell, it must initially be delivered into the cell and then, once in the cell, ultimately reside in the nucleus.

As used herein, the term "genetic therapy" involves the transfer of heterologous DNA to cells of a mammal, particularly a human, with a disorder or conditions for which therapy or diagnosis is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product; it may encode a product, such as a peptide or RNA that in some manner mediates, directly or indirectly, expression of a therapeutic product. Genetic therapy may also be used to deliver nucleic acid encoding a gene product to replace a defective gene or supplement a gene product produced by the mammal or the cell in which it is introduced. The introduced nucleic acid may encode a therapeutic compound, such as a growth factor inhibitor thereof, or a tumor necrosis factor or inhibitor thereof, such as a receptor therefore, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof.

As used herein, the term "gene" or "recombinant gene" refers to a nucleic acid comprising an open reading frame encoding a polypeptide, including both exon and (optionally) intron sequences.

As used herein, the term "heterologous nucleic acid sequence" is typically DNA that encodes RNA and proteins that are not normally produced in vivo by the cell in which it is expressed or that mediates or encodes mediators that alter expression of endogenous DNA by affecting transcription, translation, or other regulatable biochemical processes. A heterologous nucleic acid sequence may also be referred to as foreign DNA. Any DNA that one of skill in the art would recognize or consider as heterologous or foreign to the cell in which it is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

As use herein, the terms "homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

As used herein, the term "neurological disorder" includes a disease, disorder, or condition which directly or indirectly affects the normal functioning or anatomy of a subject's nervous system. The term "stroke" is art-recognized and includes sudden diminution or loss of consciousness, sensation and voluntary motion caused by rupture or obstruction (for example, by a blood clot) of an artery of the brain. "Traumatic brain injury" is art-recognized and includes the condition in which a traumatic blow to the head causes damage to the brain or connecting spinal cord, with or without penetrating the skull. Usually, the initial trauma can result in expanding hematoma, subarachnoid hemorrhage, cerebral edema, raised intracranial pressure, and cerebral hypoxia, which can, in turn, lead to severe secondary events due to low cerebral blood flow.

As used herein, the term "neuronal migration" refers to the ability of neuronal cells to migrate or neuronal processes to migrate such as an axonal or dendritic migration.

As used herein, the phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

As used herein, the phrases "systemic administration," "administered systemically," "peripheral administration" and "administered peripherally" as used herein mean the administration of a compound, drug or other material other than directly into a target tissue (e.g., the central nervous system), such that it enters the animal's system and, thus, is subject to metabolism and other like processes, for example, subcutaneous administration.

As use herein, the term "patient" or "subject" or "animal" or "host" refers to any mammal. The subject may be a human, but can also be a mammal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

As used herein, the term "peripheral nervous system (PNS) neurons" includes the neurons which reside or extend outside of the CNS. PNS is intended to include the neurons commonly understood as categorized in the peripheral nervous system, including sensory neurons and motor neurons.

As used herein, the terms "polynucleotide sequence" and "nucleotide sequence" are also used interchangeably herein.

As used herein, the terms "peptide" or "polypeptide" are used interchangeably herein and refer to compounds consisting of from about 2 to about 90 amino acid residues, inclusive, wherein the amino group of one amino acid is linked to the carboxyl group of another amino acid by a peptide bond. A peptide can be, for example, derived or removed from a native protein by enzymatic or chemical cleavage, or can be prepared using conventional peptide synthesis techniques (e.g., solid phase synthesis) or molecular biology techniques (see Sambrook et al., MOLECULAR CLONING: LAB. MANUAL (Cold Spring Harbor Press, Cold Spring Harbor, N.Y., 1989)). A "peptide" can comprise any suitable L- and/or D-amino acid, for example, common a-amino acids (e.g., alanine, glycine, valine), non-a-amino acids (e.g., P-alanine, 4-aminobutyric acid, 6aminocaproic acid, sarcosine, statine), and unusual amino acids (e.g., citrulline, homocitruline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and means for adding or removing protecting groups are known in the art. See, e.g., Green & Wuts, PROTECTING GROUPS IN ORGANIC SYNTHESIS (John Wiley & Sons, 1991). The functional groups of a peptide can also be derivatized (e.g., alkylated) using art-known methods.

Peptides can be synthesized and assembled into libraries comprising a few too many discrete molecular species. Such libraries can be prepared using well-known methods of combinatorial chemistry, and can be screened as described herein or using other suitable methods to determine if the library comprises peptides which can antagonize CSPG-PTPσ interaction. Such peptide antagonists can then be isolated by suitable means.

As used herein, the term "peptidomimetic", refers to a protein-like molecule designed to mimic a peptide. Peptidomimetics typically arise either from modification of an existing peptide, or by designing similar systems that mimic peptides, such as peptoids and β-peptides. Irrespective of the approach, the altered chemical structure is designed to advantageously adjust the molecular properties such as, stability or biological activity. These modifications involve changes to the peptide that do not occur naturally (such as altered backbones and the incorporation of nonnatural amino acids).

As used herein, the term "progenitor cells" are cells produced during differentiation of a stem cell that have some, but not all, of the characteristics of their terminally-differentiated progeny. Defined progenitor cells, such as "neural progenitor cells," are committed to a lineage, but not to a specific or terminally differentiated cell type.

As used herein, the term "stem cell" means a cell that can undergo self-renewal (i.e., progeny with the same differentiation potential) and also produce progeny cells that are more restricted in differentiation potential. Within the context of the invention, a stem cell would also encompass a more differentiated cell that has dedifferentiated, for example, by nuclear transfer, by fusions with a more primitive stem cell, by introduction of specific transcription factors, or by culture under specific conditions. See, for example, Wilmut et al., Nature, 385:810-813 (1997); Ying et al., Nature, 416:545-548 (2002); Guan et al., Nature, 440:1199-1203 (2006); Takahashi et al., Cell, 126:663-676 (2006); Okita et al., Nature, 448:313-317 (2007); and Takahashi et al., Cell, 131:861-872 (2007).

As used herein, the term "retraction" refers to the receding of the axon away from the site of injury, such as from where the glial scar forms. Here, the end of regenerating axons stop extending and become dystrophic. These dystrophic ends then can recede further from the glial scar and the site of injury.

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

As used herein, the term "recombinant," as used herein, means that a protein is derived from a prokaryotic or eukaryotic expression system.

As used herein, the term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as cells of epithelial cells. The term also covers so-called "leaky" promoters, which regulate expression of a selected nucleic acid primarily in one tissue, but cause expression in other tissues as well. The term "transfection" is used to refer to the uptake of foreign DNA by a cell. A cell has been "transfected" when exogenous DNA has been introduced inside the cell membrane. A number of transfection techniques are generally known in the art. See, e.g., Graham et al., Virology 52:456 (1973); Sambrook et al., Molecular Cloning: A Laboratory Manual (1989); Davis et al., Basic Methods in Molecular Biology (1986); Chu et al., Gene 13:197 (1981). Such techniques can be used to introduce one or more exogenous DNA moieties, such as a nucleotide integration vector and other nucleic acid molecules, into suitable host cells. The term captures chemical, electrical, and viral-mediated transfection procedures.

As used herein, the terms "transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence), which controls the expression of the recombinant gene in a cell-type in which expression is intended. It will also be understood that the recombinant gene can be under the control of transcriptional regulatory sequences which are the same or which are different from those sequences, which control transcription of the naturally occurring form of a protein.

As used herein, the term "vector" refers to a nucleic acid molecule capable of transporting another nucleic acid to which it has been linked. Preferred vectors are those capable of one or more of, autonomous replication and expression of nucleic acids to which they are linked. Vectors capable of directing the expression of genes to which they are operatively linked are referred to herein as "expression vectors".

As used herein, the term "wild type" refers to the naturally-occurring polynucleotide sequence encoding a protein, or a portion thereof, or protein sequence, or portion thereof, respectively, as it normally exists in vivo. As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The agents, compounds, compositions, antibodies, etc. used in the methods described herein are considered to be purified and/or isolated prior to their use. Purified materials are typically "substantially pure", meaning that a nucleic acid, polypeptide or fragment thereof, or other molecule has been separated from the components that naturally accompany it. Typically, the polypeptide is substantially pure when it is at least 60%, 70%, 80%, 90%, 95%, or even 99%, by weight, free from the proteins and other organic molecules with which it is associated naturally. For example, a substantially pure polypeptide may be obtained by extraction from a natural source, by expression of a recombinant nucleic acid in a cell that does not normally express that protein, or by chemical synthesis. "Isolated materials" have been removed from their natural location and environment. In the case of an isolated or purified domain or protein fragment, the domain or fragment is substantially free from amino acid sequences that flank the protein in the naturally-occurring sequence. The term "isolated DNA" means DNA has been substantially freed of the genes that flank the given DNA in the naturally occurring genome. Thus, the term "isolated DNA" encompasses, for example, cDNA, cloned genomic DNA, and synthetic DNA.

As used herein, the terms "portion", "fragment", "variant", "derivative" and "analog", when referring to a polypeptide of the present invention include any polypeptide that retains at least some biological activity referred to herein (e.g., inhibition of an interaction such as binding). Polypeptides as described herein may include portion, fragment, variant, or derivative molecules without limitation, as long as the polypeptide still serves its function.

Polypeptides or portions thereof of the present invention may include proteolytic fragments, deletion fragments and in particular, or fragments that more easily reach the site of action when delivered to an animal.

This application relates to compositions and methods for inhibiting and/or reducing the activity, signaling, and/or function of leukocyte-common antigen related (LAR) family of phosphatases, such as LAR and receptor protein tyrosine phosphatase sigma (PTPσ), and to methods and compositions of treating diseases, disorders, and/or conditions associated with activation and signaling of LAR family phosphatases, such as LAR and RPTPσ.

The LAR family of phosphatases consists of three members: LAR itself, receptor protein tyrosine phosphatase Sigma (PTPσ) and receptor protein tyrosine phosphatase delta (PTPδ). PTPσ and PTPf (LAR itself) have been implicated as receptors for chondroitin sulfate proteoglycans (CSPG), a principal constituent of the glial scar and perineuronal net. The sugar side chains of CSPGs can bind to LAR and PTPσ expressed by cells, such as neural cells, and inhibit neural cell growth, plasticity, regeneration and sprouting failure in the neural cells.

It was found that PTPσ knockout neurons showed decreased inhibition in various CSPG mediated assays and showed increased regeneration following neurological injury, such as following spinal cord injury and optic nerve crush. The results in the LAR knockout remained inconclusive, with both increased and decreased regenerative phenotypes being found. Since CSPGs are the primary impediment to regeneration and plasticity in the injured adult nervous system, functional inhibitors of these LAR family of phosphatases can be used as a therapeutic to promote neural cell growth, plasticity, regeneration and sprouting.

Accordingly, some embodiments described herein relate to methods of promoting growth, motility, survival, and/or plasticity of a cell that expresses a LAR family phosphatase (e.g., neural cells, neural progenitor cells, neural stem cells, or endothelial cells) that are and/or can potentially be activated by proteoglycans, such as CSPGs. The method can include administering to the cell an amount of a therapeutic agent effective to inhibit one or more of, catalytic activity, signaling, and/or function of the LAR family phosphatases. The inhibition of activity, signaling, and/or function of the LAR family phosphatases can be used to promote cell growth, motility, survival and plasticity in these cells.

In certain embodiments, cells that express a LAR family phosphatase include neural cells and glial cells. Other examples of cells include endothelial cells. Still other examples of cells that express a LAR family phosphatase, which can be activated by a proteoglycan can be readily screened using known assays.

The activity, signaling, and/or function of the LAR family phosphatases can be suppressed, inhibited, and/or blocked in several ways including: direct inhibition of the activity of the intracellular domain of the LAR family phosphatases (e.g., by using small molecules, peptidomimetics, or dominant negative polypeptides); activation of genes and/or proteins that inhibit one or more of, the activity, signaling, and/or function of the intracellular domain of the LAR family phosphatases (e.g., by increasing the expression or activity of the genes and/or proteins); inhibition of genes and/or proteins that are downstream mediators of the LAR family phosphatases (e.g., by blocking the expression and/or activity of the mediator genes and/or proteins); introduction of genes and/or proteins that negatively regulate one or more of, activity, signaling, and/or function of LAR family phosphatases (e.g., by using recombinant gene expression vectors, recombinant viral vectors or recombinant polypeptides); or gene replacement with, for instance, a hypomorphic mutant of the LAR family phosphatases (e.g., by homologous recombination, overexpression using recombinant gene expression or viral vectors, or mutagenesis).

The therapeutic agent that inhibits or reduces one or more of the activity, signaling, and/or function of the LAR family phosphatase can include an agent that decreases and/or suppresses the activity, signaling, and/or function of the LAR family phosphatase without inhibiting binding to or activation the LAR family phosphatases by proteoglycans, such as CSPG. Such agents can be delivered intracellularly and once delivered intracellularly promote the intrinsic growth capability of a cell, such as a neuron, activate the growth pathway of neurons (e.g., CNS), and are capable of producing a neurosalutary effect.

The neurosalutary effect can include a response or result favorable to the health or function of a neuron, of a part of the nervous system, or of the nervous system generally. Examples of such effects include improvements in the ability of a neuron or portion of the nervous system to resist insult, to regenerate, to maintain desirable function, to grow or to survive. The neurosalutary effect can include producing or effecting such a response or improvement in function or resilience within a component of the nervous system. Examples of producing a neurosalutary effect would include stimulating axonal outgrowth after injury to a neuron; rendering a neuron resistant to apoptosis; rendering a neuron resistant to a toxic compound such as β-amyloid, ammonia, or other neurotoxins; reversing age-related neuronal atrophy or loss of function; reversing age-related loss of cholinergic innervation, reversing and/or reducing dieback, and/or promoting neural sprouting.

One potential mechanism for regulation, modulation, and/or inhibition of LAR family of phosphatases involves dimerization of the intracellular portion of the LAR family of phosphatases. In contrast to receptor tyrosine kinases, which are active as dimers and inactive as monomers, several protein tyrosine phosphatases (PTPs) are inactive in the dimerized state and active as monomers. These include PTPalpha, PTP1B and CD45. Each of these molecules can be crystalized in both their active monomeric form and inactive dimeric form. In addition, LAR and CD45 demonstrate homophillic binding under specific oxidative conditions, while PTPσ can dimerize in response to ligand binding. This suggests that ligands to LAR family of phosphatases can direct the activation state of LAR family of phosphatase, such as LAR and PTPσ. Therefore, mimicking dimerization with intracellular-targeted therapies can directly inactivate LAR family of phosphatases without alteration of the extracellular matrix or other ligands.

We found that peptide mimetics of the intracellular portion of the LAR family of phosphatase when delivered into a neural cell can inhibit and/or reduce LAR activity induced by CSPG activation. Intracelluar inhibition of LAR family activity, signaling, and/or function in response to CSPG activation was found to promote neural cell outgrowth, including restoration of growth cone motility, extension of processes, sprouting, and promotion of neural cell survival and plasticity as well as inhibit neural cell dieback.

In one embodiment, the therapeutic agent that inhibits or reduces one or more of the activity, signaling, and/or function of the LAR family phosphatase, can include a therapeutic peptide or small molecule that binds to and/or complexes with the intracellular domain of at least one LAR family phosphatase to inhibit the activity, signaling, and/or function of the LAR family phosphatase. Accordingly, therapeutic peptides or small molecules that binds to and/or complexes with the intracellular domain of at least one LAR family phosphatase of neural cells can be used to promote cell growth, motility, survival and plasticity of these cells.

In some embodiments, the therapeutic agent can be a peptide mimetic of the wedged shaped domain (i.e., wedge domain) of the intracellular catalytic domain of the LAR family phosphatases. Structural and sequence analysis has revealed that all members of the LAR family contain a conserved 24 amino acid wedge-shaped helix-loop-helix motif in the first intracellular catalytic domain that can potentially mediate homo/heterophilic receptor interaction. Table 1 lists the amino acid sequences of intracellular portions of the LAR family phosphatase members that contain the wedge domain. The 24 amino acid wedge domain of these intracellular portions of LAR family phosphatases is identified by underlining. While the specific structure of the wedge domain is conserved through most LAR family wedge domains, the exact amino acids that make up the wedge domains vary between individual proteins and sub-families.

target proteins, such as phosphatase targets; (ii) interfere with activity promoting intermolecular interactions between the PTP and another domain contained in the PTP, such as the catalytically inactive second phosphatase domain D2; prevent access of proteins to the active phosphatase site; (iii) out-compete normal interactors of the wedge domain; and/or (iv) sterically inhibit phosphatase activity.

In some embodiments, the peptide mimetic (i.e., therapeutic peptide) can include, consist essentially, and/or consist of about 10 to about 20 amino acids and have an amino acid sequence that is at least about 65%, at least about 70%, at least about 75%, at least about 80%, at least about 85%, at least about 90%, at least about 95%, or about 100% homologous to an about 10 to about 20 consecutive amino acid portion of the amino acid sequence of the wedge domains of LAR family phosphatases.

In other embodiments, the therapeutic peptide can include, consist essentially, and/or consist of about 10 to about 20 amino acids and have an amino acid sequence that

TABLE 1

LAR Wedge Domain Alignment

| Mouse | 1338 PIPIT<u>DLADNIERLKANDGKLFSQEYESI</u>DPGQ | 1370 SEQ ID NO: 1 |
|---|---|---|
| Rat | 1338 PIPIT<u>DLADNIERLKANDGKLFSQEYESI</u>DPGQ | 1370 SEQ ID NO: 2 |
| Human | 1347 PIPIT<u>DLADNIERLKANDGKLFSQEYESI</u>DPGQ | 1379 SEQ ID NO: 3 |

PTPσ Wedge Domain Alignment

| Mouse | 1347 PIPIT<u>DMAEHMERLKANDSLKLSQEYESI</u>DPGQ | 1379 SEQ ID NO: 4 |
|---|---|---|
| Rat | 1303 PIPIT<u>DMAEHMERLKANDSLKLSQEYESI</u>DPGQ | 1335 SEQ ID NO: 5 |
| Human | 1368 PIPIA<u>DMAEHTERLKANDSLKLSQEYESI</u>DPGQ | 1400 SEQ ID NO: 6 |

PTPδ Wedge Domain Alignment

| Mouse | 1326 PIPIL<u>ELADHIERLKANDNLKFSQEYESI</u>DPGQ | 1379 SEQ ID NO: 7 |
|---|---|---|
| Human | 1335 PIPIL<u>ELADHIERLKANDNLKFSQEYESI</u>DPGQ | 1367 SEQ ID NO: 8 |

Wedge domains of specific LAR family members were found to engage in homophilic interaction or binding with their specific LAR family member. For example, the wedge domain of LAR was able to specifically interact with full length LAR, and not other family members such as PTPσ, in pull-down assays. In addition, in vitro binding assays showed that wedge domain peptides (wedge domain+HIV-TAT) of PTPmu and LAR specifically homophillically aggregated instead of binding promiscuously with each other. Of particular interest, the wedge domain of LAR was unable to bind to sigma, showing specificity even between similar family members.

Peptide mimetics of these wedge domains of the LAR family of phosphatase when expressed in cells (e.g., neural cells) or conjugated to an intracellular transport moiety can therefore be used to abolish LAR family signaling in a neural cell activated with CSPG and promote cell growth, motility, and survival. Binding of these therapeutic peptides to their specific PTP's intact wedge domain can potentially: (i) interfere with the ability for that PTP to interact with is at least about 65%, at least about 70%, at least about 75%, at least about 80%, at least about 85%, at least about 90%, at least about 95%, or about 100% homologous to about 10 to about 20 consecutive amino acids of the wedge domain of PTPσ. We found that a peptide (e.g., therapeutic peptide) corresponding to or substantially homologous to the wedge domain of PTPσ with a cytosolic-carrier was able to relieve CSPG-mediated inhibition, allowing neurons to advance on CSPG substrates instead of typical inhibition. This effect was dose dependent and reliant on the responding cell expressing PTPσ. Astrocytes, which do not express PTPσ at the protein level, do not respond to peptide inactivation, while satellite glia, which do express PTPσ, do respond to peptide. Additionally, this peptide can be given systemically to promote plasticity and functional recovery following severe spinal cord injury.

As shown in Table 2, the wedge domain sequence of PTPσ is highly conserved among higher mammals, with only a single amino acid change in mouse and rats (Threonine to Methithione at position 6) preventing 100% homology.

TABLE 2

Wedge Domain Alignment

```
          0                   1                   2
          1 2 3 4 5 6 7 8 9 0 1 2 3 4 5 6 7 8 9 0 1 2 3 4
```

| Sequence | Organism | SEQ ID |
|---|---|---|
| D L A E H T E H L K A N D N L K  S Q E Y E S | Xenopus | SEQ ID NO: 9 |
| D   H T E H       L K A N D N L K L S Q E Y E S I | Green anole | SEQ ID NO: 10 |
| E L A E H T E L L K A N D N L K L S Q E Y E S I | Zebrafish | SEQ ID NO: 11 |
| E L A E H T E L L K A N D N L K L S Q E Y E S I | Talapia | SEQ ID NO: 12 |
| E L A E H T E H L K A N D N L K L S Q E Y E S I | Chicken | SEQ ID NO: 13 |
| E L A E H T E H L K A N D N L K L S Q E Y E S I | Finch | SEQ ID NO: 14 |
| E L A E H T D H L K A N D N L K L S Q E Y E S I | Platypus | SEQ ID NO: 15 |
| E M A E H T E H L K A N D N L K L S Q E Y E S I | Tazmanian Devil | SEQ ID NO: 16 |
| D M A E H T E R L K A N D S L K L S Q E Y E S I | Ferret | SEQ ID NO: 17 |
| D M A E H T E R L K A N D S L K L S Q E Y E S I | Bush-Baby | SEQ ID NO: 18 |
| D M A E H T E R L K A N D S L K L S Q E Y E S I | Marmoset | SEQ ID NO: 19 |
| D M A E H M E R L K A N D S L K L S Q E Y E S I | RAT | SEQ ID NO: 20 |
| D M A E H M E R L K A N D S L K L S Q E Y E S I | Mouse | SEQ ID NO: 21 |
| D M A E H T E R L K A N D S L K L S Q E Y E S I | Dog | SEQ ID NO: 22 |
| D M A E H T E R L K A N D S L K L S Q E Y E S I | Pig | SEQ ID NO: 23 |
| D M A E H T E R L K A N D S L K L S Q E Y E S I | Cow | SEQ ID NO: 24 |
| D M A E H T E R L K A N D S L K L S Q E Y E S I | Sheep | SEQ ID NO: 25 |
| D M A E H T E R L K A N D S L K L S Q E Y E S I | Killer Whale | SEQ ID NO: 26 |
| D M A E H T E R L K A N D S L K L S Q E Y E S I | Squirrel Monkey | SEQ ID NO: 27 |
| D M A E H T E R L K A N D S L K L S Q E Y E S I | Baboon | SEQ ID NO: 28 |
| D M A E H T E R L K A N D S L K L S Q E Y E S I | Gorilla | SEQ ID NO: 29 |
| D M A E H T E R L K A N D S L K L S Q E Y E S I | Gibbon | SEQ ID NO: 30 |
| D M A E H T E R L K A N D S L K L S Q E Y E S I | Macaque | SEQ ID NO: 31 |
| D M A E H T E R L K A N D S L K L S Q E Y E S I | Chimpanzee | SEQ ID NO: 32 |
| D M A E H T E R L K A N D S L K L S Q E Y E S I | Human | SEQ ID NO: 33 |

TABLE 2-continued

Wedge Domain Alignment

```
0         1         2
1234567890123456789 01234
```

| | | |
|---|---|---|
| D L A D N I E R L K A N D G L K F S Q E Y E S I | LAR (Lar family) | SEQ ID NO: 34 |
| E L A D H I E R L K A N D N L K F S Q E Y E S I | Delta (Lar family) | SEQ ID NO: 35 |
| K L E E E I N R R N A D D N K I F R E E F N A L | ptp alpha | SEQ ID NO: 36 |

As shown in Table 2, the first alpha helix of the wedge domain of PTPσ includes amino acids 1-10, the turn region includes amino acids 11-14, and the second alpha helix includes amino acids 15-24. For example, the first alpha helix of the wedge domain of human PTPσ has the amino acid sequence of DMAEHTERLK (SEQ ID NO: 67), the turn has the amino acid sequence of ANDS (SEQ ID NO: 68), and the second alpha helix has the amino acid sequence of LKLSQEYESI (SEQ ID NO: 69).

The wedge domain also shares sequence homology with the other members of the LAR family, LAR and PTPdelta. It is likely that these amino acids are necessary for the overall structure of the wedge domain. Conserved amino acids include an alanine at position 13, which marks the end of the first alpha helix and the start of the turn, making it likely to be necessary for general wedge size and structure.

Since the general secondary and tertiary structures of the wedge domain remain consistent through most receptor PTPs, several conservative substitutions can be made to a therapeutic peptide targeting the PTPσ wedge domain to obtain similar results. Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue such as lysine, arginine or histidine for another, and/or the substitution of one acidic residue, such as aspartic acid or glutamic acid for another.

These conservative substitutions can occur in the non-unique domains in either alpha helix or the turn, specifically positions 1-3 and 7-10 in the first alpha helix; 12 and 13 in the turn; and 15, 16, 18-24 in the second alpha helix. These amino acids may be necessary to the overall structure of the wedge domain, but not necessary for specificity of binding of wedge to PTPG.

The unique amino acids to PTPG, particularly the amino acids expressed differentially in PTPG vs LAR, were found to be necessary for specificity of wedge domain binding. These include an EH domain in the first alpha helix position 4 and 5 followed by a threonine or a metathione (rat and mouse substitution) at position 6. In the turn, there is a unique serine at position 14 in all higher mammals. Finally, there is a unique leucine at position 17 in the second alpha helix. The potential roles of these unique amino acids will be discussed below.

The serine residue in the turn at position 14 is of particular interest due to its location in the wedge domain. This amino acid, located in the turn between alpha helixes, is slightly extended from the general secondary and tertiary structure of PTPG, making it available for binding interactions. In addition, serine, due to its hydroxyl group and the polarity it contains, is known to facilitate several homophillic and heterophillic binding events, such as hydrogen binding between adjacent serines. Serines are also known to undergo various modifications, such as phosphorylation, making the likelihood of its necessity for specificity high. It is possible that smaller peptides that focus on the turn in the wedge domain and include the conserved serine may offer greater stability with similar function. Such peptides can be synthesized as loops, with cysteine's on either end to created di-sulfide bonds.

The unique amino acids in the first alpha helix include glutamic acid at position 4, histidine at position 5 and threonine or metathione at position 6. Although the histidine is implicated in the consensus wedge domain, it is not found in LAR, PTPdelta, PTPmu or CD45. As all three of these amino acids are either charged or polar, it is likely that either this sequence or one of its components is necessary for PTPσ wedge specificity.

Additionally, the second alpha helix contains a unique leucine at position 17. Leucines have been implicated as the critical adhesive molecules for the three dimensional structure of leucine zippers. In these molecules, which are structurally similar to wedge domains, leucines of opposing alpha helixes, located at approximately 7 intervals, interact with hydrophobic regions of the opposing alpha helix. As there is also a Leucine in the first alpha helix, located at position 9, it is believed that this unique leucine is necessary for the overall three-dimensional structural integrity of the PTPσ wedge.

Accordingly, in other embodiments, the therapeutic peptide can include, consist essentially of, or consist of about 14 to about 20 amino acids and include the amino acid sequence EHX$_1$ERLKANDSLKL (SEQ ID NO: 37), wherein X$_1$ is T or M. A therapeutic peptide including SEQ ID NO: 37 can include at least one, at least two, at least three, at least four, or at least five conservative substitutions so that the therapeutic peptide has an amino acid sequence that is at least about 65%, at least about 70%, at least about 75%, at least about 80%, at least about 85%, at least about 90%, or at least about 95% homologous to SEQ ID NO: 37.

In some embodiments, the conservative substitutions can be of amino acid residues 4E, 5R, 6L, 7K, 9N, 10D, 12L, or 13K of SEQ ID NO: 37. By way of example, amino acid residue 4E can be substituted with D or Q, amino acid residue 5R can be substituted with H, L, or K, amino acid residue 6L can be substituted with I, V, or M, amino acid residue 7K can be substituted with R or H, amino acid residue 9N can be substituted with E or D, amino acid residue 10 D can be substituted with E or N, amino acid residue 12L can be substituted with I, V, or M, and/or amino acid residue 13K can be substituted with R or H.

The therapeutic peptides described herein can be subject to other various changes, substitutions, insertions, and deletions where such changes provide for certain advantages in its use. In this regard, therapeutic peptides that bind to and/or complex with a wedge domain of the LAR family phosphatase can correspond to or be substantially homologous with, rather than be identical to, the sequence of a recited polypeptide where one or more changes are made and it retains the ability to inhibits or reduces one or more of the activity, signaling, and/or function of the LAR family phosphatase function.

The therapeutic polypeptide can be in any of a variety of forms of polypeptide derivatives, that include amides, conjugates with proteins, cyclized polypeptides, polymerized polypeptides, analogs, fragments, chemically modified polypeptides, and the like derivatives.

It will be appreciated that the conservative substitution can also include the use of a chemically derivatized residue in place of a non-derivatized residue provided that such peptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides described herein also include any polypeptide having one or more additions and/or deletions or residues relative to the sequence of a polypeptide whose sequence is shown herein, so long as the requisite activity is maintained.

In still other embodiments, the therapeutic agent can be mimetic or competitive inhibitor of a downstream protein that is activated by LAR family phosphatase. Several downstream proteins and pathways have been shown to act downstream of the LAR family outside of phosphatase activity. Of these, Caskin (Ckn) and LAR-interacting protein α (Liprin-α) have roles in both synapse formation and axonal guidance.

mCkn1 directly binds mLAR and mPTPRδ, and mCkn2 directly binds mLAR and mPTPσ in a yeast two hybrid interaction system. Ckn's interaction with LAR family phosphatases was mapped to a region containing two sterile-alpha motifs (SAM domains) domain account for the phenotype. The first SAM domain is conserved between Ckn family members.

Accordingly, in some embodiments, the therapeutic agent can be a peptide mimetic or competitive inhibitor of Ckn that inhibits LAR family phosphatase/Ckn binding and mitigates downstream LAR family signaling. The peptide can have an amino acid sequence that is at least about 75%, at least about 80%, at least about 85%, at least about 90%, or at least about 95% homologous to about 10 to about 30 consecutive amino acids of a portion of mCkn1 and mCkn2. Examples of peptides that have amino acid sequence that is substantially homologous to about 10 to about 30 consecutive amino acids of a portion of mCkn1 and mCkn2 are SEQ ID NO: 38, SEQ ID NO: 39, and SEQ ID NO: 40.

In other embodiments, the therapeutic agent can be a peptide mimetic or competitive inhibitor of Liprin-α that that inhibits LAR family phosphatase/Liprin-α binding, and mitigates downstream LAR family signaling. Liprin family members play critical roles in the development and maintenance of synapses. Liprin-α may act in signal transduction downstream of LAR phosphatases. Yeast-2-hybrid interaction screening implicates the first SAM domain of Liprin-α family members as the binding region for LAR phosphatase family members. The peptide can have an amino acid sequence that is substantially homologous to about 10 to about 30 consecutive amino acids of a portion of Liprin-α. An example of a peptide that has an amino acid sequence that is substantially homologous to about 10 to about 30 consecutive amino acids of a portion of Liprin-α is SEQ ID NO: 41.

Similar to the therapeutic peptides described above that bind to or complex with the wedge domain, the therapeutic polypeptides that are mimetics or competitive inhibitors with mCkn1, mCkn2, or Liprin-α can be subject to various changes, substitutions, insertions, and deletions where such changes provide for certain advantages in its use. For example, the therapeutic polypeptide can be in any of a variety of forms of polypeptide derivatives, that include amides, conjugates with proteins, cyclized polypeptides, polymerized polypeptides, analogs, fragments, chemically modified polypeptides, and the like derivatives.

One or more of peptides of the therapeutic peptides described herein can also be modified by natural processes, such as posttranslational processing, and/or by chemical modification techniques, which are known in the art. Modifications may occur in the peptide including the peptide backbone, the amino acid side-chains and the amino or carboxy termini. It will be appreciated that the same type of modification may be present in the same or varying degrees at several sites in a given peptide. Modifications comprise for example, without limitation, acetylation, acylation, addition of acetomidomethyl (Acm) group, ADP-ribosylation, amidation, covalent attachment to fiavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, 2nd Ed., T. E. Creighton, W. H. Freeman and Company, New-York, 1993).

Peptides and/or proteins described herein may also include, for example, biologically active mutants, variants, fragments, chimeras, and analogues; fragments encompass amino acid sequences having truncations of one or more amino acids, wherein the truncation may originate from the amino terminus (N-terminus), carboxy terminus (C-terminus), or from the interior of the protein. Analogues of the invention involve an insertion or a substitution of one or more amino acids. Variants, mutants, fragments, chimeras and analogues may function as inhibitors of the LAR family phosphatases (without being restricted to the present examples).

The therapeutic polypeptides described herein may be prepared by methods known to those skilled in the art. The peptides and/or proteins may be prepared using recombinant DNA. For example, one preparation can include cultivating a host cell (bacterial or eukaryotic) under conditions, which provide for the expression of peptides and/or proteins within the cell.

The purification of the polypeptides may be done by affinity methods, ion exchange chromatography, size exclusion chromatography, hydrophobicity or other purification technique typically used for protein purification. The purification step can be performed under non-denaturing conditions. On the other hand, if a denaturing step is required, the protein may be renatured using techniques known in the art.

In some embodiments, the therapeutic peptides described herein can include additional residues that may be added at either terminus of a polypeptide for the purpose of providing a "linker" by which the polypeptides can be conveniently linked and/or affixed to other polypeptides, proteins, detectable moieties, labels, solid matrices, or carriers.

Amino acid residue linkers are usually at least one residue and can be 40 or more residues, more often 1 to 10 residues. Typical amino acid residues used for linking are glycine, tyrosine, cysteine, lysine, glutamic and aspartic acid, or the like. In addition, a subject polypeptide can differ by the sequence being modified by terminal-NH2 acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

In some embodiments, the linker can be a flexible peptide linker that links the therapeutic peptide to other polypeptides, proteins, and/or molecules, such as detectable moieties, labels, solid matrices, or carriers. A flexible peptide linker can be about 20 or fewer amino acids in length. For example, a peptide linker can contain about 12 or fewer amino acid residues, e.g., 3, 4, 5, 6, 7, 8, 9, 10, 11, and 12. In some cases, a peptide linker comprises two or more of the following amino acids: glycine, serine, alanine, and threonine.

In some embodiments, a therapeutic agent comprising the therapeutic peptides described herein can be provided in the form of a conjugate protein or drug delivery construct includes at least a transport subdomain(s) or moiety(ies) (i.e., transport moieties) that is linked to the therapeutic peptide. The transport moieties can facilitate uptake of the therapeutic polypeptides into a mammalian (i.e., human or animal) tissue or cell (e.g., neural cell). The transport moieties can be covalently linked to the therapeutic polypeptides. The covalent link can include a peptide bond or a labile bond (e.g., a bond readily cleavable or subject to chemical change in the interior target cell environment). Additionally, the transport moieties can be cross-linked (e.g., chemically cross-linked, UV cross-linked) to the therapeutic polypeptide. The transport moieties can also be linked to the therapeutic polypeptide with linking polypeptide described herein.

The transport moieties can be repeated more than once in the therapeutic agent. The repetition of a transport moiety may affect (e.g., increase) the uptake of the peptides and/or proteins by a desired cell. The transport moiety may also be located either at the amino-terminal region of therapeutic peptide or at its carboxy-terminal region or at both regions.

In one embodiment, the transport moiety can include at least one transport peptide sequence that allows the therapeutic polypeptide once linked to the transport moiety to penetrate into the cell by a receptor-independent mechanism. In one example, the transport peptide is a synthetic peptide that contains a Tat-mediated protein delivery sequence and at least one of SEQ ID NOs: 9-33 and 37-41. These peptides can have, respectively, the amino acid sequences of SEQ ID NOs: 42-66 and 70-74.

Other examples of known transport moieties, subdomains and the like are described in, for example, Canadian patent document No. 2,301,157 (conjugates containing homeodomain of antennapedia) as well as in U.S. Pat. Nos. 5,652,122, 5,670,617, 5,674,980, 5,747,641, and 5,804,604, all of which are incorporated herein by reference in their entirety, (conjugates containing amino acids of Tat HIV protein; herpes simplex virus-1 DNA binding protein VP22, a Histidine tag ranging in length from 4 to 30 histidine repeats, or a variation derivative or homologue thereof capable of facilitating uptake of the active cargo moiety by a receptor independent process.

A 16 amino acid region of the third alpha-helix of antennapedia homeodomain has also been shown to enable proteins (made as fusion proteins) to cross cellular membranes (PCT international publication number WO 99/11809 and Canadian application No.: 2,301,157. Similarly, HIV Tat protein was shown to be able to cross cellular membranes.

In addition, the transport moiety(ies) can include polypeptides having a basic amino acid rich region covalently linked to an active agent moiety (e.g., intracellular domain-containing fragments inhibitor peptide). As used herein, the term "basic amino acid rich region" relates to a region of a protein with a high content of the basic amino acids such as arginine, histidine, asparagine, glutamine, lysine. A "basic amino acid rich region" may have, for example 15% or more of basic amino acid. In some instance, a "basic amino acid rich region" may have less than 15% of basic amino acids and still function as a transport agent region. In other instances, a basic amino acid region will have 30% or more of basic amino acids.

The transport moiety(ies) may further include a proline rich region. As used herein, the term proline rich region refers to a region of a polypeptide with 5% or more (up to 100%) of proline in its sequence. In some instance, a proline rich region may have between 5% and 15% of prolines. Additionally, a proline rich region refers to a region, of a polypeptide containing more prolines than what is generally observed in naturally occurring proteins (e.g., proteins encoded by the human genome). Proline rich regions of this application can function as a transport agent region.

In one embodiment, the therapeutic peptide described herein can be non-covalently linked to a transduction agent. An example of a non-covalently linked polypeptide transduction agent is the Chariot protein delivery system (See U.S. Pat. No. 6,841,535; *J Biol Chem* 274(35):24941-24946; and *Nature Biotec.* 19:1173-1176, all herein incorporated by reference in their entirety).

In other embodiments, the therapeutic peptides can be expressed in cells being treated using gene therapy to inhibit LAR family signaling. The gene therapy can use a vector including a nucleotide encoding the therapeutic peptides. A "vector" (sometimes referred to as gene delivery or gene transfer "vehicle") refers to a macromolecule or complex of molecules comprising a polynucleotide to be delivered to the cell. The polynucleotide to be delivered may comprise a coding sequence of interest in gene therapy. Vectors include, for example, viral vectors (such as adenoviruses (Ad), adeno-associated viruses (AAV), and retroviruses), liposomes and other lipid-containing complexes, and other macromolecular complexes capable of mediating delivery of a polynucleotide to a target cell.

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available.

Vectors for use herein include viral vectors, lipid based vectors and other non-viral vectors that are capable of delivering a nucleotide encoding the therapeutic peptides described herein to the target cells. The vector can be a targeted vector, especially a targeted vector that preferentially binds to neurons and. Viral vectors for use in the application can include those that exhibit low toxicity to a target cell and induce production of therapeutically useful quantities of the therapeutic peptide in a cell specific manner.

Examples of viral vectors are those derived from adenovirus (Ad) or adeno-associated virus (AAV). Both human and non-human viral vectors can be used and the recombinant viral vector can be replication-defective in humans. Where the vector is an adenovirus, the vector can comprise a polynucleotide having a promoter operably linked to a gene encoding the therapeutic peptides and is replication-defective in humans.

Other viral vectors that can be used herein include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid.

Retroviruses, such as C-type retroviruses and lentiviruses, might also be used in the application. For example, retroviral vectors may be based on murine leukemia virus (MLV). See, e.g., Hu and Pathak, Pharmacol. Rev. 52:493-511, 2000 and Fong et al., Crit. Rev. Ther. Drug Carrier Syst. 17:1-60, 2000. MLV-based vectors may contain up to 8 kb of heterologous (therapeutic) DNA in place of the viral genes. The heterologous DNA may include a tissue-specific promoter and a nucleic acid encoding the therapeutic peptide. In methods of delivery to neural cells, it may also encode a ligand to a tissue specific receptor.

Additional retroviral vectors that might be used are replication-defective lentivirus-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells.

Lentiviral vectors for use in the application may be derived from human and non-human (including SIV) lentiviruses. Examples of lentiviral vectors include nucleic acid sequences required for vector propagation as well as a tissue-specific promoter operably linked to a therapeutic peptide encoding nucleic acid. These former may include the viral LTRs, a primer binding site, a polypurine tract, att sites, and an encapsidation site.

In some aspects, a lentiviral vector can be employed. Lentiviruses have proven capable of transducing different types of CNS neurons (Azzouz et al., (2002) *J Neurosci.* 22: 10302-12) and may be used in some embodiments because of their large cloning capacity.

A lentiviral vector may be packaged into any lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN) might also be used in the application. Use of alphaviruses is described in Lundstrom, K., Intervirology 43:247-257, 2000 and Perri et al., Journal of Virology 74:9802-9807, 2000.

Recombinant, replication-defective alphavirus vectors are advantageous because they are capable of high-level heterologous (therapeutic) gene expression, and can infect a wide target cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell.

In many of the viral vectors compatible with methods of the application, more than one promoter can be included in the vector to allow more than one heterologous gene to be expressed by the vector. Further, the vector can comprise a sequence, which encodes a signal peptide or other moiety, which facilitates expression of the therapeutic peptide from the target cell.

To combine advantageous properties of two viral vector systems, hybrid viral vectors may be used to deliver a nucleic acid encoding a therapeutic peptide to a target neuron, cell, or tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18:176-186, 2000. Retroviral genomes contained within an adenovirus may integrate within the target cell genome and effect stable gene expression.

Other nucleotide sequence elements, which facilitate expression of the therapeutic peptide and cloning of the vector are further contemplated. For example, the presence of enhancers upstream of the promoter or terminators downstream of the coding region, for example, can facilitate expression.

In accordance with another embodiment, a tissue-specific promoter can be fused to nucleotides encoding the therapeutic peptides described herein. By fusing such tissue specific promoter within the adenoviral construct, transgene expression is limited to a particular tissue. The efficacy of gene expression and degree of specificity provided by tissue specific promoters can be determined, using the recombinant adenoviral system of the present application. Neuron specific promoters, such as the platelet-derived growth factor β-chain (PDGF-β) promoter and vectors, are well known in the art.

In addition to viral vector-based methods, non-viral methods may also be used to introduce a nucleic acid encoding a therapeutic peptide into a target cell. A review of non-viral methods of gene delivery is provided in Nishikawa and Huang, Human Gene Ther. 12:861-870, 2001. An example of a non-viral gene delivery method according to the application employs plasmid DNA to introduce a nucleic acid encoding a therapeutic peptide into a cell. Plasmid-based gene delivery methods are generally known in the art.

Synthetic gene transfer molecules can be designed to form multimolecular aggregates with plasmid DNA. These aggregates can be designed to bind to a target cell. Cationic amphiphiles, including lipopolyamines and cationic lipids, may be used to provide receptor-independent nucleic acid transfer into target cells.

In addition, preformed cationic liposomes or cationic lipids may be mixed with plasmid DNA to generate cell-transfecting complexes. Methods involving cationic lipid formulations are reviewed in Felgner et al., Ann. N.Y. Acad. Sci. 772:126-139, 1995 and Lasic and Templeton, Adv. Drug Delivery Rev. 20:221-266, 1996. For gene delivery, DNA may also be coupled to an amphipathic cationic peptide (Fominaya et al., J. Gene Med. 2:455-464, 2000).

Methods that involve both viral and non-viral based components may be used according to the application. For example, an Epstein Barr virus (EBV)-based plasmid for therapeutic gene delivery is described in Cui et al., Gene Therapy 8:1508-1513, 2001. Additionally, a method involving a DNA/ligand/polycationic adjunct coupled to an adenovirus is described in Curiel, D. T., Nat. Immun. 13:141-164, 1994.

Additionally, the nucleic acid encoding the therapeutic peptides can be introduced into the target cell by transfecting the target cells using electroporation techniques. Electroporation techniques are well known and can be used to facilitate transfection of cells using plasmid DNA.

Vectors that encode the expression of the therapeutic peptides can be delivered in vivo to the target cell in the form of an injectable preparation containing pharmaceutically acceptable carrier, such as saline, as necessary. Other pharmaceutical carriers, formulations and dosages can also be used in accordance with the present application.

Where the target cell includes a neuron being treated, such as quiescent or dormant neurons, the vector can be delivered by direct injection at an amount sufficient for the therapeutic peptide to be expressed to a degree, which allows for highly effective therapy. By injecting the vector directly into or about the periphery of the neuron, it is possible to target the vector transfection rather effectively, and to minimize loss of the recombinant vectors. This type of injection enables local transfection of a desired number of cells, especially at a site of CNS injury, thereby maximizing therapeutic efficacy of gene transfer, and minimizing the possibility of an inflammatory response to viral proteins. Other methods of administering the vector to the target cells can be used and will depend on the specific vector employed.

The therapeutic peptide can be expressed for any suitable length of time within the target cell, including transient expression and stable, long-term expression. In one aspect of the application, the nucleic acid encoding the therapeutic peptide will be expressed in therapeutic amounts for a defined length of time effective to induce activity and growth of the transfected cells. In another aspect of the application, the nucleic acid encoding the therapeutic peptide will be expressed in therapeutic amounts for a defined length of time effective to restore lost function in a targeted neuron after a CNS injury.

A therapeutic amount is an amount, which is capable of producing a medically desirable result in a treated animal or human. As is well known in the medical arts, dosage for any one animal or human depends on many factors, including the subject's size, body surface area, age, the particular composition to be administered, sex, time and route of administration, general health, and other drugs being administered concurrently. Specific dosages of proteins and nucleic acids can be determined readily determined by one skilled in the art using the experimental methods described below.

The therapeutic agents described herein may further be modified (e.g., chemically modified). Such modification may be designed to facilitate manipulation or purification of the molecule, to increase solubility of the molecule, to facilitate administration, targeting to the desired location, to increase or decrease half life. A number of such modifications are known in the art and can be applied by the skilled practitioner.

In some embodiments, the therapeutic agents and pharmaceutical compositions comprising the therapeutic agents described herein may be delivered to neurons of the CNS and/or the PNS. Such neurons may be injured or diseased. Such neurons may alternatively be healthy, uninjured neurons. Such neurons may be located at the site of injury, or at a site incident to the injury. The neurons to be targeted for therapeutic administration, delivery/contact of the agents and compositions described herein will be neurons from which neuronal outgrowth is thought to prove beneficial to the subject. Such determination is within the ability of the skilled practitioner through no more than routine experimentation.

The therapeutic agents and therapeutic pharmaceutical compositions described herein may also be delivered to non-neuronal cells of the CNS and/or the PNS, such as to non-neuronal cells that provide support to neural cells. Such cells include, without limitation, glial cells (e.g., astrocytes, oligodendrocytes, ependymal cells, radial glial in the CNS; and Schwann cells, satellite glial cells, enteric glial cells n the PNS).

In the methods of treatment disclosed herein, a therapeutically effective amount of the therapeutic agent is administered to the subject. In one embodiment, a formulation including the therapeutic agent is administered to the subject in the period from the time of, for example, an injury to the nervous system up to about 100 hours after the injury has occurred, for example within 24, 12, or 6 hours from the time of injury.

In one embodiment, the administration is specific for one or more specific locations within the subject's nervous system. The preferred mode of administration can vary depending upon the particular agent chosen and the particular target.

When the therapeutic agents are delivered to a subject, they can be administered by any suitable route, including, for example, orally (e.g., in capsules, suspensions or tablets), systemically, or by parenteral administration. Parenteral administration can include, for example, intramuscular, intravenous, intraarticular, intraarterial, intrathecal, subcutaneous, or intraperitoneal administration. The agent can also be administered orally, transdermally, topically, by inhalation (e.g., intrabronchial, intranasal, oral inhalation or intranasal drops) or rectally. Administration can be local or systemic as indicated.

Both local and systemic administration are contemplated herein. Desirable features of local administration include achieving effective local concentrations of the therapeutic agent as well as avoiding adverse side effects from systemic administration of the therapeutic agent. In one embodiment, the therapeutic agent can be administered by introduction into the cerebrospinal fluid of the subject. In certain aspects, the therapeutic agent can be introduced into a cerebral ventricle, the lumbar area, or the cisterna magna. In another aspect, the therapeutic agent can be introduced locally, such as into the site of nerve or cord injury, into a site of pain or neural degeneration, or intraocularly to contact neuroretinal cells.

The pharmaceutically acceptable formulations can be suspended in aqueous vehicles and introduced through conventional hypodermic needles or using infusion pumps.

In another embodiment, the therapeutic agent can be administered into a subject intrathecally. As used herein, the term "intrathecal administration" is intended to include delivering a therapeutic agent directly into the cerebrospinal fluid of a subject, by techniques including lateral cerebroventricular injection through a burrhole or cisternal or lumbar puncture or the like (described in Lazorthes et al., 1991, and Ommaya, 1984, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The ten-n "cerebral ventricle" is intended to include the cavities in the brain that are continuous with the central canal of the spinal cord. Administration of therapeutic agent to any of the above mentioned sites can be achieved by direct injection of the therapeutic agent or by the use of infusion pumps. Implantable or external pumps and catheter may be used.

For injection, therapeutic agent can be formulated in liquid solutions, typically in physiologically compatible buffers such as Hank's solution or Ringer's solution. In addition, the therapeutic agent may be formulated in solid form and re-dissolved or suspended immediately prior to use. Lyophilized forms are also included. The injection can be, for example, in the form of a bolus injection or continuous infusion (such as using infusion pumps) of the therapeutic agent.

In one embodiment, the therapeutic agent can be administered by lateral cerebroventricular injection into the brain of a subject, usually within 100 hours of when an injury (resulting in a condition characterized by aberrant axonal outgrowth of central nervous system neurons) occurs (such as within 6, 12, 24 or 100 hours, inclusive, from the time of the injury). The injection can be made, for example, through a burr hole made in the subject's skull. In another embodiment, the therapeutic agent can be administered through a surgically inserted shunt into the cerebral ventricle of a subject, usually within 100 hours of when an injury occurs (e.g., within 6, 12 or 24 hours, inclusive, from the time of the injury). For example, the injection can be made into the lateral ventricles, which are larger, even though injection into the third and fourth smaller ventricles can also be made. In yet another embodiment, the therapeutic agent can be administered by injection into the cisterna magna, or lumbar area of a subject, within 100 hours of when an injury occurs (such as within 6, 12, or 24 hours, inclusive, from the time of the injury).

An additional means of administration to intracranial tissue involves application to the olfactory epithelium, with subsequent transmission to the olfactory bulb and transport to more proximal portions of the brain. Such administration can be by nebulized or aerosolized preparations.

In another embodiment, the therapeutic agent can be administered to a subject at the site of injury, usually within 100 hours of when an injury occurs (e.g., within 6, 12, or 24 hours, inclusive, of the time of the injury).

In a further embodiment, ophthalmic compositions of the therapeutic agents described herein are used to prevent or reduce damage to retinal and optic nerve head tissues, as well as to enhance functional recovery after damage to ocular tissues. Ophthalmic conditions that may be treated include, but are not limited to, retinopathies (including diabetic retinopathy and retrolental fibroplasia), macular degeneration, ocular ischemia, glaucoma. Other conditions to be treated with the methods of the invention include damage associated with injuries to ophthalmic tissues, such as ischemia reperfusion injuries, photochemical injuries, and injuries associated with ocular surgery, particularly injuries to the retina or optic nerve head by exposure to light or surgical instruments. The ophthalmic compositions may also be used as an adjunct to ophthalmic surgery, such as by vitreal or subconjunctival injection following ophthalmic surgery. The therapeutic agents may be used for acute treatment of temporary conditions, or may be administered chronically, especially in the case of degenerative disease. The ophthalmic compositions may also be used prophylactically, especially prior to ocular surgery or noninvasive ophthalmic procedures or other types of surgery.

In some embodiments, the therapeutic agent can administered to a subject for an extended period of time to produce optimum axonal outgrowth or sprouting and/or inhibit dieback. Sustained contact with the active compound can be achieved, for example, by repeated administration of the active compound(s) over a period of time, such as one week, several weeks, one month or longer. The pharmaceutically acceptable formulation used to administer the therapeutic agent(s) can also be formulated to provide sustained delivery of the active compound to a subject. For example, the formulation may deliver the active compound for at least one, two, three, or four weeks, inclusive, following initial administration to the subject. For example, a subject to be treated in accordance with the present invention is treated with the active compound for at least 30 days (either by repeated administration or by use of a sustained delivery system, or both).

Sustained delivery of the therapeutic agent can be demonstrated by, for example, the continued therapeutic effect of the therapeutic agent over time (such as sustained delivery of the agents can be demonstrated by continued axonal growth in CNS neurons in a subject). Alternatively, sustained delivery of the therapeutic agent may be demonstrated by detecting the presence of the therapeutic agents in vivo over time.

Approaches for sustained delivery include use of a polymeric capsule, a minipump to deliver the formulation, a biodegradable implant, or implanted transgenic autologous cells (see U.S. Pat. No. 6,214,622). Implantable infusion pump systems (e.g., INFUSAID pumps (Towanda, Pa.)); see Zierski et al., 1988; Kanoff, 1994) and osmotic pumps (sold by Alza Corporation) are available commercially and otherwise known in the art. Another mode of administration is via an implantable, externally programmable infusion pump. Infusion pump systems and reservoir systems are also described in, e.g., U.S. Pat. Nos. 5,368,562 and 4,731,058.

Vectors encoding the therapeutic peptides can often be administered less frequently than other types of therapeutics. For example, an effective amount of such a vector can range from about 0.01 mg/kg to about 5 or 10 mg/kg, inclusive; administered daily, weekly, biweekly, monthly or less frequently.

The ability to deliver or express the therapeutic peptides allows for cell activity modulation in a number of different cell types. The therapeutic peptides can be expressed, for example, in a heart cell via heart specific promotors for modulating the contractions (or excitability) of the heart, in the spinal cord via HB9 promotor for modulating motor neuron activity after spinal cord injury, and in neural cells or brain areas affected by degenerative diseases, such as Parkinson's disease, to control excitability in the brain area of nerve cells of choice.

In some embodiments, neurons derived from the central or peripheral nervous system can be contacted with the therapeutic agents ex vivo to promote axonal outgrowth in vitro. Accordingly, neurons can be isolated from a subject and grown in vitro, using techniques well known in the art, and then treated to modulate axonal outgrowth. Briefly, a neuronal culture can be obtained by allowing neurons to migrate out of fragments of neural tissue adhering to a suitable substrate (such as a culture dish) or by disaggregating the tissue, such as mechanically or enzymatically, to produce a suspension of neurons. For example, the enzymes trypsin, collagenase, elastase, hyaluronidase, DNase, pronase, dispase, or various combinations thereof can be used. Methods for isolating neuronal tissue and the disaggregation of tissue to obtain isolated cells are described in Freshney, CULTURE OF ANIMAL CELLS, A MANUAL OF BASIC TECHNIQUE, (3rd ed., 1994). Such cells can be subsequently contacted with the therapeutic agents in amounts and for a duration of time as described above. Once modulation of axonal outgrowth has been achieved in the neurons, these cells can be re-administered to the subject, such as by implantation.

The ability of an agent to promote neural regeneration in a subject may be assessed using any of a variety of known procedures and assays. For example, the ability of an agent to re-establish neural connectivity and/or function after an injury, may be determined histologically (either by slicing neuronal tissue and looking at neuronal branching, or by showing cytoplasmic transport of dyes). Agents may also be assessed by monitoring the ability of the agent to fully or partially restore the electroretinogram after damage to the neural retina or optic nerve; or to fully or partially restore a pupillary response to light in the damaged eye.

Other tests that may be used include standard tests of neurological function in human subjects or in animal models of spinal injury (such as standard reflex testing, urologic tests, urodynamic testing, tests for deep and superficial pain appreciation, propnoceptive placing of the hind limbs, ambulation, and evoked potential testing). In addition, nerve impulse conduction can be measured in a subject, such as by measuring conduct action potentials, as an indication of the production of a neurosalutary effect.

Animal models that can be used herein include the rat model of partial transaction, which tests how well a compound can enhance the survival and sprouting of the intact remaining fragment of an almost fully-transected cord. Accordingly, after administration of a candidate agent these animals may be evaluated for recovery of a certain function, such as how well the rats may manipulate food pellets with their forearms (to which the relevant cord had been cut 97%).

Another animal model that can be used in the assays includes the rat model of stroke. Administration to these animals of the agents can be used to assess whether a given compound, route of administration, or dosage provides a neuroregenerative effect, such as increasing the level of function, or increasing the rate of regaining function or the degree of retention of function in the test animals.

Standard neurological evaluations used to assess progress in human patients after a stroke may also be used to evaluate the ability of an agent to produce a neurosalutary effect in a subject. Such standard neurological evaluations are routine in the medical arts, and are described in, for example, "Guide to Clinical Neurobiology" Edited by Mohr and Gautier (Churchill Livingstone Inc. 1995).

In some embodiments, the therapeutic agents can be used to treat diseases, disorders, or condition associated with elements of the nervous system, including the central, somatic, autonomic, sympathetic and parasympathetic components of the nervous system, neurosensory tissues within the eye, ear, nose, mouth or other organs, as well as glial tissues associated with neuronal cells and structures. Neurological disorders may be caused by an injury to a neuron, such as a mechanical injury or an injury due to a toxic compound, by the abnormal growth or development of a neuron, or by the misregulation, such as downregulation, of an activity of a neuron. In one embodiment, the therapeutic agents can be applied to a damaged nerve, the site of nerve damage or the site of nerve damage repair. In some embodiments, the therapeutic agents are applied to the site of primary nerve repair. The damage to the nerve can represent a nerve transection (neurotmesis), wherein the nerve is partially or fully severed or a small region damaged and surgically removed.

Neurological disorders can detrimentally affect nervous system functions such as the sensory function (the ability to sense changes within the body and the outside environment); the integrative function (the ability to interpret the changes); and the motor function (the ability to respond to the interpretation by initiating an action such as a muscular contraction or glandular secretion).

Examples of neurological disorders include traumatic or toxic injuries to peripheral or cranial nerves, spinal cord or to the brain, cranial nerves, traumatic brain injury, stroke, cerebral aneurism, and spinal cord injury. Other neurological disorders include cognitive and neurodegenerative disorders such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, hereditary motor and sensory neuropathy (Charcot-Marie-Tooth disease), diabetic neuropathy, progressive supranuclear palsy, epilepsy, and Jakob-Creutzfieldt disease. Autonomic function disorders include hypertension and sleep disorders.

Also to be treated with therapeutic agents described herein are neuropsychiatric disorders, such as depression, schizophrenia, schizoaffective disorder, Korsakoff's psychosis, mania, anxiety disorders, or phobic disorders, learning or memory disorders (such as amnesia and age-related memory loss), attention deficit disorder, dysthymic disorder, major depressive disorder, mania, obsessive-compulsive disorder, psychoactive substance use disorders, anxiety, phobias, panic disorder, bipolar affective disorder, psychogenic pain syndromes, and eating disorders. Other examples of neurological disorders include injuries to the nervous system due to an infectious disease (such as meningitis, high fevers of various etiologies, HIV, syphilis, or post-polio syndrome) and injuries to the nervous system due to electricity (including contact with electricity or lightning, and complications from electro-convulsive psychiatric therapy). Neurological disorders associated with ophthalmic conditions include retina and optic nerve damage, glaucoma and age related macular degeneration.

The developing brain is a target for neurotoxicity in the developing central nervous system through many stages of pregnancy as well as during infancy and early childhood, and the methods of the invention may be utilized in preventing or treating neurological deficits in embryos or fetuses in utero, in premature infants, or in children with need of such treatment, including those with neurological birth defects. Further neurological disorders include, for example, those listed in HARRISON'S PRINCIPLES OF INTERNAL MEDICINE (Braunwald et al., McGraw-Hill, 2001) and in the AMERICAN PSYCHIATRIC ASSOCIATION'S DIAGNOSTIC AND STATISTICAL MANUAL OF MENTAL DISORDERS DSM-IV (American Psychiatric Press, 2000).

The therapeutic agents described herein can also be used in a method of to treat a medical condition associated with a neural injury. The medical condition can refer to any movement disorders, epilepsy, cerebrovascular diseases, autoimmune diseases, sleep disorders, autonomic disorders, urinary bladder disorders, abnormal metabolic states, disorders of the muscular system, infectious and parasitic diseases neoplasms, endocrine diseases, nutritional and metabolic diseases, immunological diseases, diseases of the blood and blood-forming organs, mental disorders, diseases of the nervous system, diseases of the sense organs, diseases of the circulatory system, diseases of the respiratory system, diseases of the digestive system, diseases of the genitourinary system, diseases of the skin and subcutaneous tissue, diseases of the musculoskeletal system and connective tissue, congenital anomalies, certain conditions originating in the perinatal period, and symptoms, signs, and ill-defined conditions.

Cerebrovascular disease treatable may be caused by conditions including, but not limited to, aneurysms, strokes, arrhythmia, myocardial infarction, ischemia reperfusion injury, and cerebral hemorrhage.

Autoimmune diseases treatable include, but are not limited to, multiple sclerosis.

Sleep disorders treatable by the present application may be caused by conditions including, but not limited to, sleep apnea and parasomnias.

Autonomic disorders treatable by the present application may be caused by conditions including, but not limited to, gastrointestinal disorders, including but not limited to gastrointestinal motility disorders, nausea, vomiting, diarrhea, chronic hiccups, gastroesphageal reflux disease, and hypersecretion of gastric acid, autonomic insufficiency; excessive epiphoresis, excessive rhinorrhea; and cardiovascular disorders including, but not limited, to cardiac dysrythmias and arrythmias, hypertension, and carotid sinus disease.

Urinary bladder disorders treatable by the present application may be caused by conditions including, but not limited to, spinal cord injury and spastic or flaccid bladder.

Abnormal metabolic states treatable by the present application may be caused by conditions including, but not limited to, hyperthyroidism or hypothyroidism. Disorders of the muscular system treatable by the present application can include, but are not limited to, muscular dystrophy, and spasms of the upper respiratory tract and face.

The therapeutic agents can also be used to treat neuropathic pain caused by conditions including, but not limited to, migraine headaches, including migraine headaches with aura, migraine headaches without aura, menstrual migraines, migraine variants, atypical migraines, complicated migraines, hemiplegic migraines, transformed migraines, and chronic daily migraines, episodic tension headaches, chronic tension headaches, analgesic rebound headaches, episodic cluster headaches, chronic cluster headaches, cluster variants, chronic paroxysmal hemicranias, hemicrania continua, post-traumatic headache, post-traumatic neck pain, post-herpetic neuralgia involving the head or face, pain from spine fracture secondary to osteoporosis, arthritis pain in the spine, headache related to cerebrovascular disease and stroke, headache due to vascular disorder, reflex sympathetic dystrophy, cervicalgia (which may be due to various causes, including, but not limited to, muscular, discogenic, or degenerative, including arthritic, posturally related, or metastatic), glossodynia, carotidynia, cricoidynia, otalgia due to middle ear lesion, gastric pain, sciatica, maxillary neuralgia, laryngeal pain, myalgia of neck muscles, trigeminal neuralgia (sometimes also termed tic douloureux), post-lumbar puncture headache, low cerebro-spinal fluid pressure headache, temporomandibular joint disorder, atypical facial pain, ciliary neuralgia, paratrigeminal neuralgia (sometimes also termed Raeder's syndrome); petrosal neuralgia, Eagle's syndrome, idiopathic intracranial hypertension, orofacial pain, myofascial pain syndrome involving the head, neck, and shoulder, chronic migraneous neuralgia, cervical headache, paratrigeminal paralysis, SPG neuralgia (sometimes also termed lower-half headache, lower facial neuralgia syndrome, Sluder's neuralgia, and Sluder's syndrome), carotidynia, vidian neuralgia, causalgia, and/or a combination of the above.

As used herein, the term "headache" can refer to migraines, tension headaches, cluster headaches, trigeminal neuralgia, secondary headaches, tension-type headaches, chronic and epsisodic headaches, medication overuse/rebound headaches, chronic paroxysmal hemicrinia headaches, hemicranias continua headaches, post-traumatic headaches, post-herpetic headaches, vascular headaches, reflex sympathetic dystrophy-related headaches, crvicalgia headaches, caroidynia headaches, sciatica headaches, trigeminal headaches, occipital headaches, maxillary headaches, chary headaches, paratrigeminal headaches, petrosal headaches, Sluder's headache, vidian headaches, low CSF pressure headaches, TMJ headaches, causalgia headaches, myofascial headaches, all primary headaches (e.g., primary stabbing headache, primary cough headache, primary exertional headache, primary headache associated with sexual activity, hypnic headache, and new daily persistent headache), all trigeminal autonomic cephalagias (e.g., episodic paroxysmal hemicranias, SUNCT, all probable TACs, and SUNA), chronic daily headaches, occipital neuralgia, atypical facial pain, neuropathic trigeminal pain, and miscellaneous-type headaches.

In still other embodiments, the therapeutic agents can be used to promote stem cell or progenitor cell survival, plasticity, and/or growth. The stem cells can include any stem cell that express an LAR phosphatase receptor, including neural stem cell or progenitor cells. The therapeutic agents can be administered to the stem cell or progenitor cells ex vivo, in vitro, or in vivo. When administered ex vivo or in vitro to the stem cells or progenitor cells, the stem cell or progenitor can then be transplanted to a subject for therapeutic applications.

For the neural stem/progenitor cell, for example, a method of transplanting a neural stem/progenitor cell(s) to a desired area that is generally used in the field of regenerative medicine may be employed in conjunction with administration of the therapeutic agent to the cells or area. More specifically, there can be exemplified, for example, a method of transplanting a neural stem/progenitor cell(s) to an area of interest by: suspending neural stem/progenitor cells in phosphate buffered saline with the therapeutic agent; and adding/injecting the resultant cell suspension to the area.

In other embodiments, the therapeutic agents described herein can be applied to a nerve graft. The graft can include any tissue intended for implantation within a human or animal. Various types of graft are encompassed within the subject invention, such as autografts, syngrafts, allografts, and xenografts. The size (e.g., length and diameter) of the graft is not critical. For example, the length of the nerve graft can be from about 1 centimeter to about 10 centimeters, or over about 10 centimeters. The diameter of the nerve graft can match that of any injured nerve or part of a nerve, as needed. The nerve graft can be a structurally complete segment of nerve to bridge a gap along the length of the recipient's nerve or to replace the distal end, i.e., for end-to-end grafting. Alternatively, the nerve graft can be a partial nerve segment, or eccentrically-shaped (e.g., a nerve flap), and intended to reconstruct a lacerated nerve that has some structural disruption, but retains its physical continuity.

When the therapeutic agents are applied to a nerve graft, the entire graft can be treated. The therapeutic agents can be applied to the entire nerve graft, en bloc. The en bloc treatment can be applied to living (fresh) or previously frozen nerve grafts. The therapeutic agents can also be applied to a nerve graft before, during, or after implantation. The therapeutic agents can be applied to any portion of the graft, such as the end or ends to be joined to the stump of a damaged nerve. If the therapeutic agent is applied to the damaged nerve, the therapeutic agent can be applied to any area of the damaged nerve that promotes repair of the damaged nerve, such as at the site of damage or adjacent to the site of damage.

The therapeutic agent can be placed in a culture medium for application to the nerve graft. The culture medium can be undefined medium, defined medium, or defined medium supplemented with serum for example. Embodiments described herein also include storage solutions for storage of nerve grafts prior to implantation. The storage solution contains a culture medium and at least one therapeutic agent. The storage solution can also include other biologically active agents, such as the growth factors described below.

In other embodiments, it is known that spinal cord injury, such as C2 hemisection, leads to an increase of inhibitory proteoglycans within the extracellular matrix and the perineuronal net ipsilateral to the hemisection, but distal to the cord lesion, at the level of the phrenic motor nucleus. As discussed in U.S. patent application Ser. No. 10/754,102, which is incorporated herein by reference, treatment with chondroitinase ABC (ChABC) degrades these potently inhibitory matrix molecules.

It is contemplated herein that enzymatically (via chondroitinase: ChABC) modifying inhibitory extracellular matrices in the PNN surrounding motor neurons combined with administration of the therapeutic agents can maximize the sprouting capacity and functional impact of remaining nerve fibers. It is further contemplated that enhancing and/or bringing about much greater total fiber sprouting combined with enhancing the physiological output of the neurons themselves will act synergistically to improve spinal cord injury. Therefore, in another embodiment, subjects can be administered chondroitinase ABC in addition to the therapeutic agents described herein to bring about an even more enhanced recovery than either treatment used alone. In some embodiments, bolus injections of ChABC into the vicinity of a CNS lesion can promote motor function in a subject.

The methods described herein can further include administration or contacting a cell (e.g., a neuron) with an agent that blocks regeneration inhibitors, e.g., a compound that inhibit myelin derived blockage of neural generation. Known inhibitors of neuronal outgrowth (e.g., of regeneration at a CNS injury site) are myelin-derived inhibitors (e.g., Nogo-A, MAG, OMgp, Ehprin B3, Sema 4D and Sema 5A), astrocyte derived inhibitors (e.g., CSPG, KSPG, Ephrin B2 and Slit), fibroblast derived inhibitors (e.g., Sema 3A). The second agent may be an antagonist to any of these inhibitors. In one embodiment, the cell is further contacted with one or more such agents. In one embodiment, the agent inhibits a myelin inhibitor of neural regeneration (e.g., myelin-associated glycoprotein (MAG), Nogo, oligodendrocyte myelin glycoprotein (OMgp)). Inhibitors of MAG are disclosed in U.S. Pat. No. 5,932,542. Inhibitors of Nogo are disclosed in U.S. Patent Application Pub No. 2009/0215691. Inhibitors of OMgp are disclosed in U.S. Patent Application Pub. No. 2008/0188411. The cell can be contacted with this agent before, after, and/or concurrently with the agent that inhibits the interaction of CSPG with PTPσ.

In some embodiments, the cell can also be contacted with agent that activates the growth pathway of neurons (e.g., CNS). Some agents include but are not limited to neurotrophic factors such as inosine, mannose, gulose, or glucose-6-phosphate, as described in Li et al., 23 J. Neurosci. 7830 (2003); Chen et al., 99 PNAS 1931 (2002); and Benowitz et al., 273 J. Biol. Chem. 29626 (1998). TGF-#946, and oncomodulin as described in Yin et al., 23 J. Neurosci. 2284 (2003), are also agents. In addition, polypeptide growth factors such as BDNF, NGF, NT-3, CNTF, LIF, and GDNF can be used. In one embodiment, the methods, which include an agent that stimulates neuronal outgrowth, further comprise contacting neurons (e.g., CNS) with a cAMP modulator that increases the concentration of intracellular cAMP (e.g., cAMP), and/or polyamines (Cal et al., 35 Neuron 711 (2002)). For example, the ability of mature rat retinal ganglionic cells to respond to mannose requires elevated cAMP (Li et. al., 2003).

The invention is further illustrated by the following example, which is not intended to limit the scope of the claims.

Example 1

This Example shows that long term exposure to CSPGs causes growth cones to collapse, stabilize and over-adhere. In this Example, a spot assay used to measure CSPG induced stabilization of adult sensory neurons.

Method

Adult female rat sensory dorsal root ganglion (DRG) neurons were obtained and grown on gradients of the chondroitin sulfate proteoglycan aggrecan as previously described. Glass bottom delta-T time-lapse dishes were coated with Poly-L-Lysine (PLL) and incubated at room temperature overnight. Spots were created by dissolving 2 mg/ml aggrecan in calcium and magnesium free hanks balanced salt solution (HBSS). Eight 2 µl dots were placed into one half of each dish and given ample time to dry onto the glass. The dishes were finally coated in 10 µg/ml laminin for 3 hours at 37° C. Following incubation, six thousand adult dissociated DRG neurons were added to each dish in neural basal-A media supplemented with Glutamax, Penn/strep and B27. The cells were allowed to grow for 4-6 days Immediately prior to the start of time lapse, the delta T dishes were sealed with a glass coverslip. 100× time-lapse microscopy was performed with a heated objective and heated stage to keep the cells at 37 degrees. Images were obtained every 30 seconds and stitched together to create a time lapse movie. Growth cone and filopodial dynamics were tracked and quantified manually with Metamorph.

Results

Figure 2:
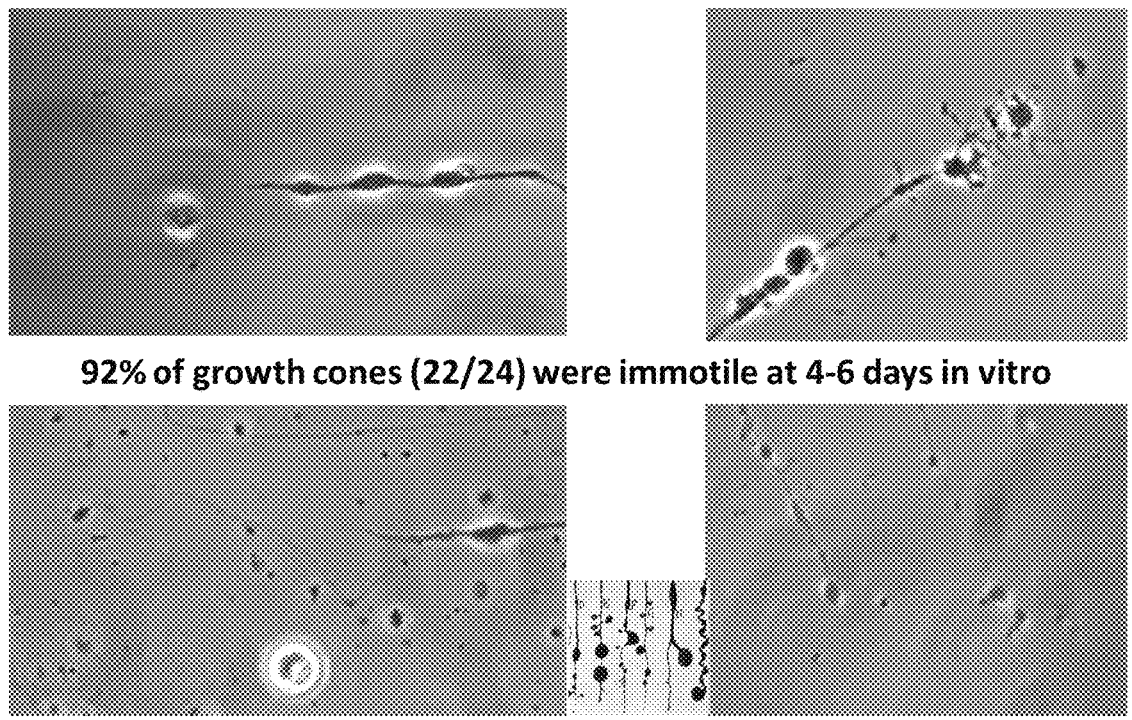
FIG. 2 illustrates photographs of growth cones of adult sensory DRG neurons in a spot assay exposed to gradient of CSPG.

FIGS. 1 and 2 show that adult sensory neurons exposed to gradients of the CSPG aggrecan stabilized at a particular region of the spot rim and over-adhered to the substrate, leading to a lack of growth cone formation, filopodial extentions and motility. 22 of 24 growth cones examined (92 percent) were stuck in place and non-motile at 4-6 days in vitro.

Example 2

This Example shows that LAR expression is higher in stabilized growth cones than motile cones. In this Example, the spot assay was conducted on glass coverslips with a few alterations from the technique used for time-lapse microscopy. Following PLL treatment, the coverslips were dried and coated with a small amount of nitrocellulose to increase adhesive interactions needed for spot formation. Following drying of nitrocellulose, 4 spots were dotted onto each coverslip (one in each quadrant) using 700 µg/ml aggrecan, 5 µg/ml laminin dissolved into HBSS. Following drying, the coverslips were coated in 5 µg/ml laminin at 37 degrees C. for 3 hours. 2,000 adult dissociated dorsal root ganglia neurons were added to each coverslip in neural basal-A media supplemented with Glutamax, Penn/strep and B27. In addition, peptides were added at the required concentration at the time of plating. Cells were allowed to grow for 5 days prior to fixation in 4% Paraformaldehyde.

Slides were fixed and stained for goat-anti PTPσ (1:100, R&D systems) and mouse anti-B$_3$Tubulin (Invitrogen, 1:500) Axons and growth cones were imaged at 100×. PTPσ density in the growth cone and axonal compartments were analyzed in ImageJ (N=40 for each dystrophic and non-dystrophic neurons).

Figure 3:
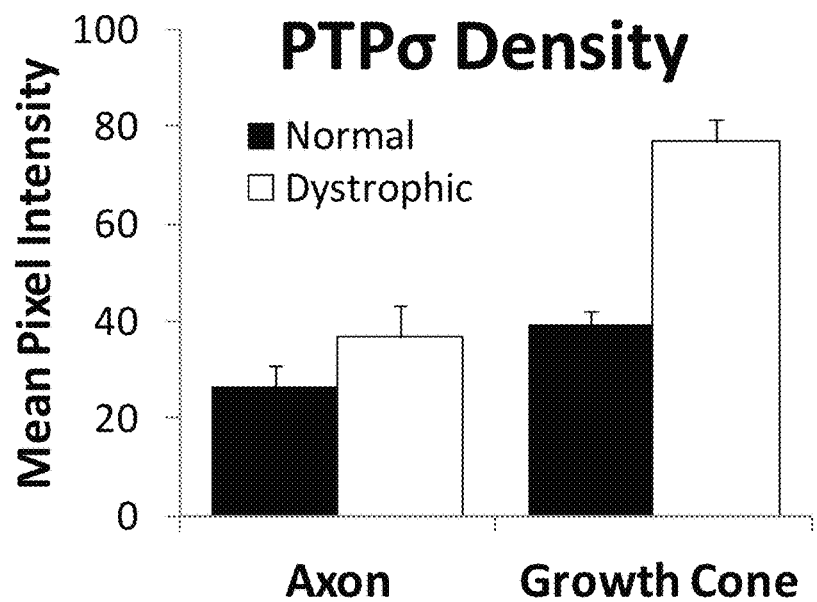
FIG. 3 illustrates a graph showing PTPσ density of normal and dystrophic axons and growth cones.

FIG. 3 shows that PTPσ density was significantly concentrated in dystrophic, stabilized growth cones vs. motile growth cones on laminin.

Example 3

Figure 4:
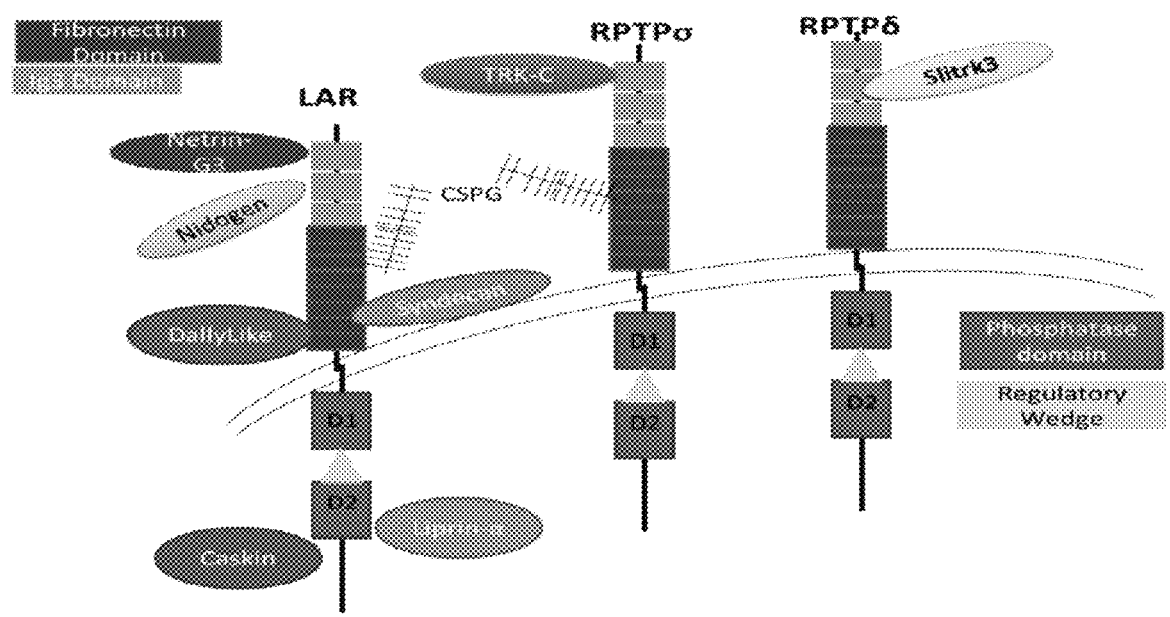
FIG. 4 illustrates a schematic diagram of the LAR family of transmembrane phosphatases, LAR, RPTPo, RPTPdelta and their signaling components.

As illustrated schematically in FIG. 4, the Leukocyte-common Antigen-Related (LAR) family of phosphatases consists of three members: LAR itself, receptor protein tyrosine phosphatase Sigma (RPTPσ) and receptor protein tyrosine phosphatase delta (RPTPδ). Recent reports have shown a binding interaction between LAR or RPTPσ and the sugar side chains of chondroitin sulfate proteoglycans (CSPGs), molecules that are highly inhibitory to neural growth, plasticity and regeneration. Furthermore, crystallography and sequence analysis shows that all three family members contain the exact same binding domain and binding pocket, providing evidence that RPTPδ may also be a functional receptor for CSPGs. Structural and sequence analysis has revealed that all members of the LAR family contain a wedge-shaped helix-loop-helix motif in the first intracellular catalytic domain that mediates homo/heterophilic receptor interaction. Using peptide mimetics of this wedge domain tagged to a cytosolic localizing TAT sequence, LAR activity was successfully abolished in neurotrophin signaling paradigms. We utilized NIH BLAST to identify the orthologous sequence in RPTPσ and RPTPδ and designed a wedge domain peptide for each target. The peptides were coined Intraceullar LAR blocking peptide (ILP), intracellular Sigma blocking peptide (ISP) and intracellular delta blocking peptide (IDP). Interestingly, this domain is highly conserved among higher vertebrates, indicating a functionally important region.

```
Rat and mouse PTPσ wedge:
                                (SEQ ID NO 20 and 21)
DMAEHMERLKANDSLKLSQEYESI.

Human PTPσ wedge:
                                (SEQ ID NO: 33)
DMAEHTERLKANDSLKLSQEYESI The peptide was tagged conjugated to HIV-TAT to
create function blocking peptides:
HIV-TAT
                                (SEQ ID NO: 53 and 54)
NH2GRKKRRQRRRCDMAEHMERLKANDSLKLSQEYESI-NH2 PTPσ mouse/rat.
                                (SEQ ID NO: 66)
NH2GRKKRRQRRRCDMAEHTERLKANDSLKLSQEYESI-NH2 PTPσ human.
                                (SEQ ID NO: 94)
NH2GRKKRRQRRRCDLADNIERLKANDGLKFSQEYESI-NHS LAR.

(SEQ ID NO: 95)
NH2GRKKRRQRRRCELADHIERLKANDNLKFSQEYESI-NH2

PTPdelta.
```

-continued (SEQ ID NO: 96)
NH$_2$GRKKRRQRRRCIREDDSLMLYALAQEKKESNMHES-NH$_2$

Scrambled Sigma.

These peptides were ordered from Genscript and dissolved in water and stored long-term at −80° C. Peptides were added to media at time of neuronal plating.

After 5 days in vitro, the cells were fixed and stained for mouse anti-B$_3$Tubulin (green). The number of processes completely spanning the gradient were counted and normalized to the number of neuronal cell bodies on each individual spot.

Results

Figure 5:
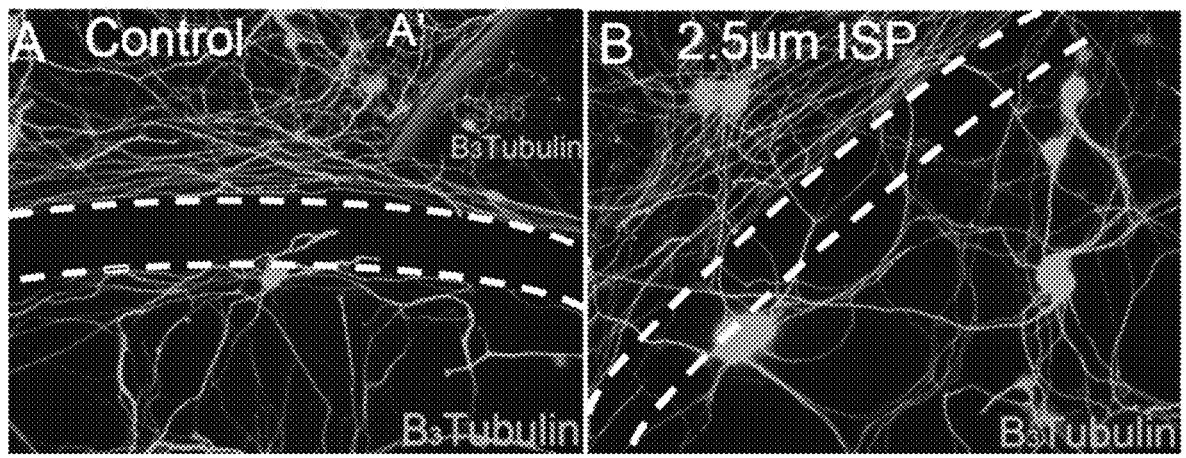
FIG. 5 illustrates a photograph of adult sensory DRG neurons in a spot assay exposed to gradients of CSPG and treated with a vehicle control or ISP.
Figure 6:
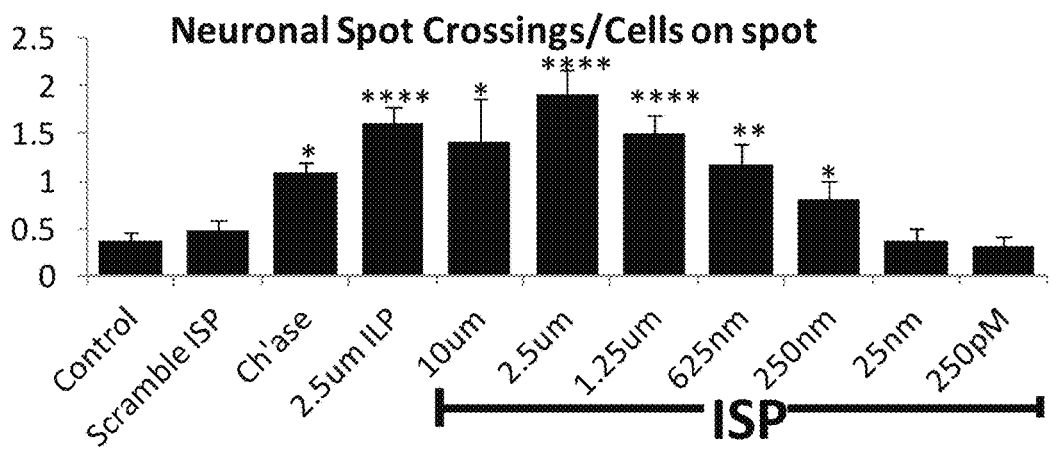
FIG. 6 illustrates a graph showing growth cone crossings of adult sensory DRG neurons in a spot assay exposed to gradients of CSPG and treated with a vehicle control or ISP.
Figures 7A, 7B:
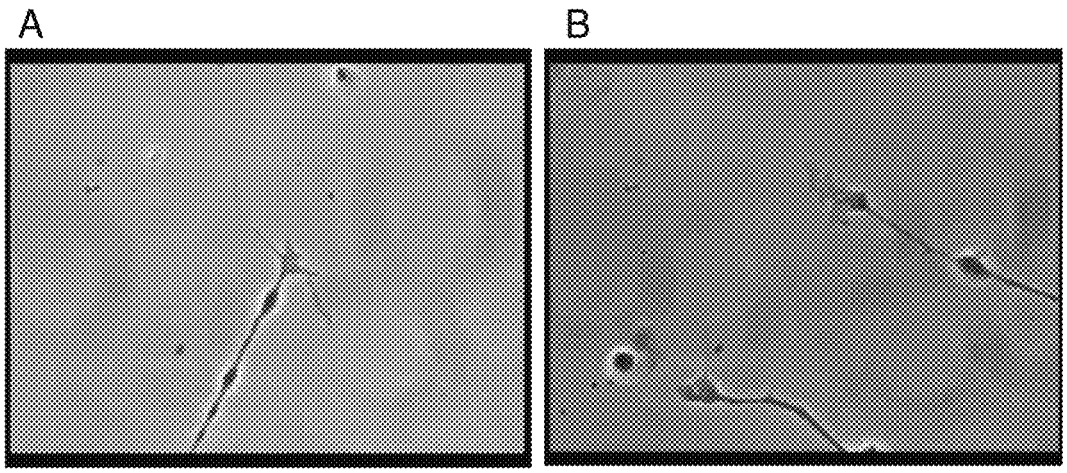
FIGS. 7(A-B) illustrate photographs showing growth cone mobility of sensory DRG neurons in a spot assay exposed to gradients of CSPG treated with a vehicle control or ISP.

FIGS. 5-7 show he wedge domain peptide for PTPσ (ISP) allows neurons to extend processes that cross CSPG gradients. The treatment was dose dependent, with the optimal crossing coming at 2.5 m. In addition, the LAR peptide (ILP) also allows neurons to traverse gradients of CSPG (FIG. 6). Neither vehicle control nor the scrambled ISP-TAT peptide allowed neuronal extensions across the gradient. In time-lapse, treatment with ISP prevented axonal stabilization and over adhesion, allowing growth cones to extend filapodia and remain motile. 65% of growth cones analyzed were still motile at 4-6 days in vitro, as opposed to 8% in the control condition.

Example 4

This Example describes methods of generating a moderate/severe contusive spinal cord injury with the Infinite Horizon device in adult female Sprague-Dawley rats for spinal cord injury (SCI) assays used in Examples 5-8. Briefly, rats were deeply anesthetized with a cocktail of ketamine/xylazine. Once under, the back was shaved and sterilized with Iodine and ethanol. Using a dorsal entry, the lumbar vertebrae 7-10 were exposed by a skin incision and at segments 8 and 9 a laminectomy was performed to expose the intact spinal cord. The spinal column and cord were stabilized in a stereotaxic frame prior to contusive imapact. Finally, rats underwent a 250 kd Infinite Horizon contusion centered at the midline with no dwell time. Following muscle suturing and skin stapling, the animals were placed on a 37° C. hot pad and allowed ample access to food and water upon awakening from surgery. Pain was monitored, and animals in distress received a low dose of Marcaine at the injection site. Saline and Gentamycin (antibiotic) were given for 5 days post-surgery to prevent bladder infections. This experiment was performed start to finish 3 times. N−=15 ISP, N=11 vehicle and N=6 ILP.

Animals were randomly divided into three groups, vehicle control, ISP, or ILP. Lyophilized ISP or ILP peptide was first dissolved in sterile water at a concentration of 2.5 mM. To create individual treatments for each animal, the peptide was further diluted to a concentration of 5 µM in a vehicle solution of 5% DMSO in sterile saline. 25 ml of each treatment (ILP, ISP or vehicle) was alliquoted into 50 individual Eppendorf tubes, each containing 500 µl. The drugs were stored at −20 and thawed immediately prior to use. Each animal received 500 µl of either vehicle, 5 µM ISP or 5 µM ILP subcutaneously into the back above the lesion each day, starting 1 day after injury and lasting 7 weeks (49 treatments, 11 µg/rat/day).

Example 5

This Example shows hindlimb movements and locomotor patterns according to the Basso, Beattie and Bresnahan scale for post-SCI locomotion of vehicle treated SCI animals and LAR peptide treated SCI animals.

Methods

Animals were allowed to freely roam on a table-top for three minutes while their hindlimb movements and locomotor patterns were being scored by a blinded observer according to the Basso, Beattie and Bresnahan scale for post-SCI locomotion (Basso et al, 1995). Behavior was performed at post injury days 1, 4, 7 and then weekly for 10 additional weeks. Statistical analysis was conducted by repeated measures 2 way Anova.

Results

Figure 9:
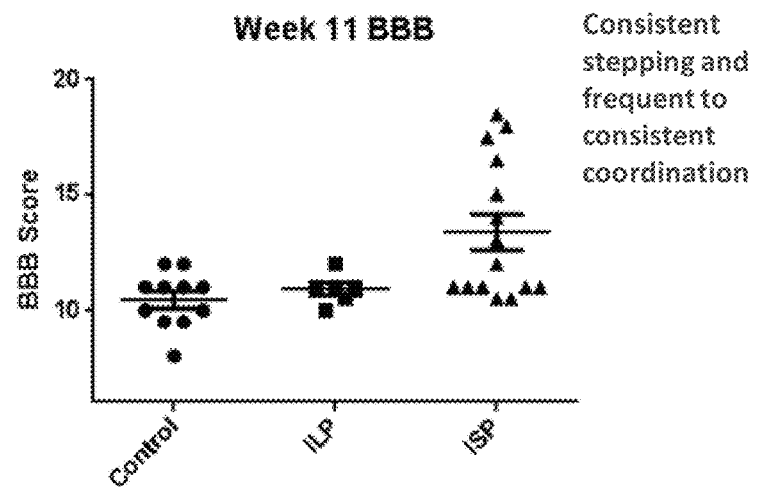
FIG. 9 illustrates a graph showing thd hindlimb Basso, Beattie and Bresnahan score for post-SCI locomotion of vehicle treated SCI animals and LAR peptide treated SCI animals at day 11.

FIGS. 8 and 9 show that following an initial period of spinal shock, all treatment groups recovered basic hindlimb movement by 2 weeks post injury, with an average BBB score of 9 (hind limb weight support without stepping). Over the course of the next 10 weeks, both the vehicle treated animals and the LAR peptide treated animals recovered only slightly beyond this point, on average regaining the ability to take the occasional weighted step. On average, ISP treated animals continued to recover, reaching a score of 12 at 6 weeks (consistent stepping with occasional hindlimb fore-limb coordination) and greater than 13 by 7 weeks (between frequent and consistent coordinatiton). Individually, animals reached a score of 19, which is near perfect locomotion with the tail held high, consistent toe clearance on steps and correct paw placement. Additional animals reached near-normal scores of 18.5 and 18. 7 of 15 animals regained at least frequent coordinated stepping.

Example 6

This Example shows the results of grid-walk test of vehicle treated SCI animals and the LAR peptide treated SCI animals.

Methods

Animals were allowed to freely roam on a wire grid (100 cm×75 cm, with 1 cm$^2$ gaps in the wire) 12 weeks after spinal cord injury. While an overhead camera tracked and calculated the total distance traveled (Ethovision), the number of foot-faults was counted manually by a blinded observer. Data is presented as total number of left and right foot-faults per meter traveled. The grid walk test was performed only once to prevent animals from training and artificially improving (rehabilitation phenomenom).

Results

Figure 10:
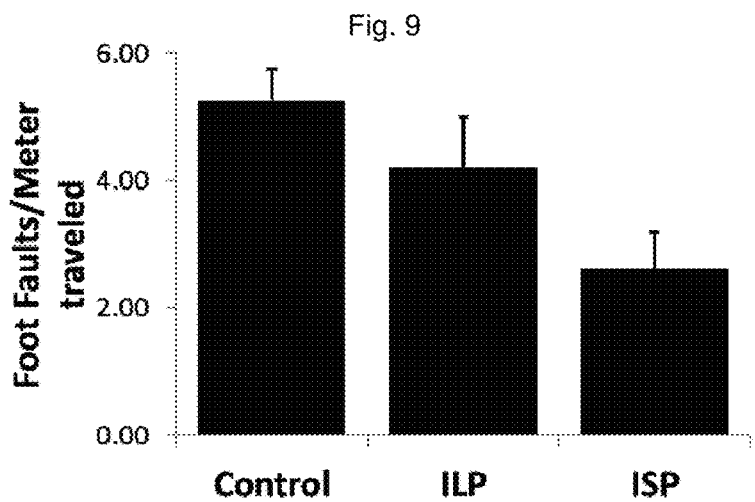
FIG. 10 illustrates a graph showing the foot fault/meter of vehicle treated SCI animals and LAR peptide treated SCI animals.
Figure 11:
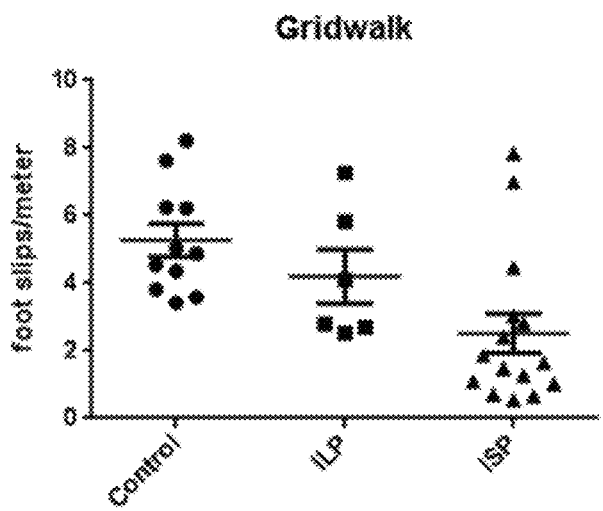
FIG. 11 illustrates a graph showing foot slips/meter of vehicle treated SCI animals and LAR peptide treated SCI animals.

The grid-walk test was used to measure recovery of sensorimotor coordination and balance. FIGS. 10 and 11 show on average, vehicle treated animals made 6 foot-faults per meter traveled on the grid. ILP treatment led to a very slight insignificant improvement in foot faults in the grid walk test. ISP treated animals made significantly fewer foot faults than vehicle treated and ILP treated animals on average. In addition, several animals made less than 3 foot faults, suggesting a near complete recovery of this behavior.

Example 7

This Example shows urinary function recovery of vehicle treated SCI animals and ISP peptide treated SCI animals.

Methods (Metabolic Cages)

Animals were placed in metabolic cages overnight for a dark cycle (16 hours). The urine was separated and collected into a syringe linked to a force transducer. The increase in force corresponding to each individual void was plotted in spike-2. The graphs were sampled into excel and manually confirmed to count the total number of voids and the average volume of each void.

(Urodynamics)

In a terminal experiment, animals were anesthetized with Urethane at 14 weeks post injury. This anesthetization prevents excessive movements while preserving bladder reflexes. A cathether was inserted through the urethra and into the bladder to allow for slow perfusion with saline. In addition, two electrodes were inserted through the vagina into the external urethral sphincter to measure muscle activity. Both muscle activity and pressure (measured through the catheter) were plotted in spike2.

Results

Figure 12:
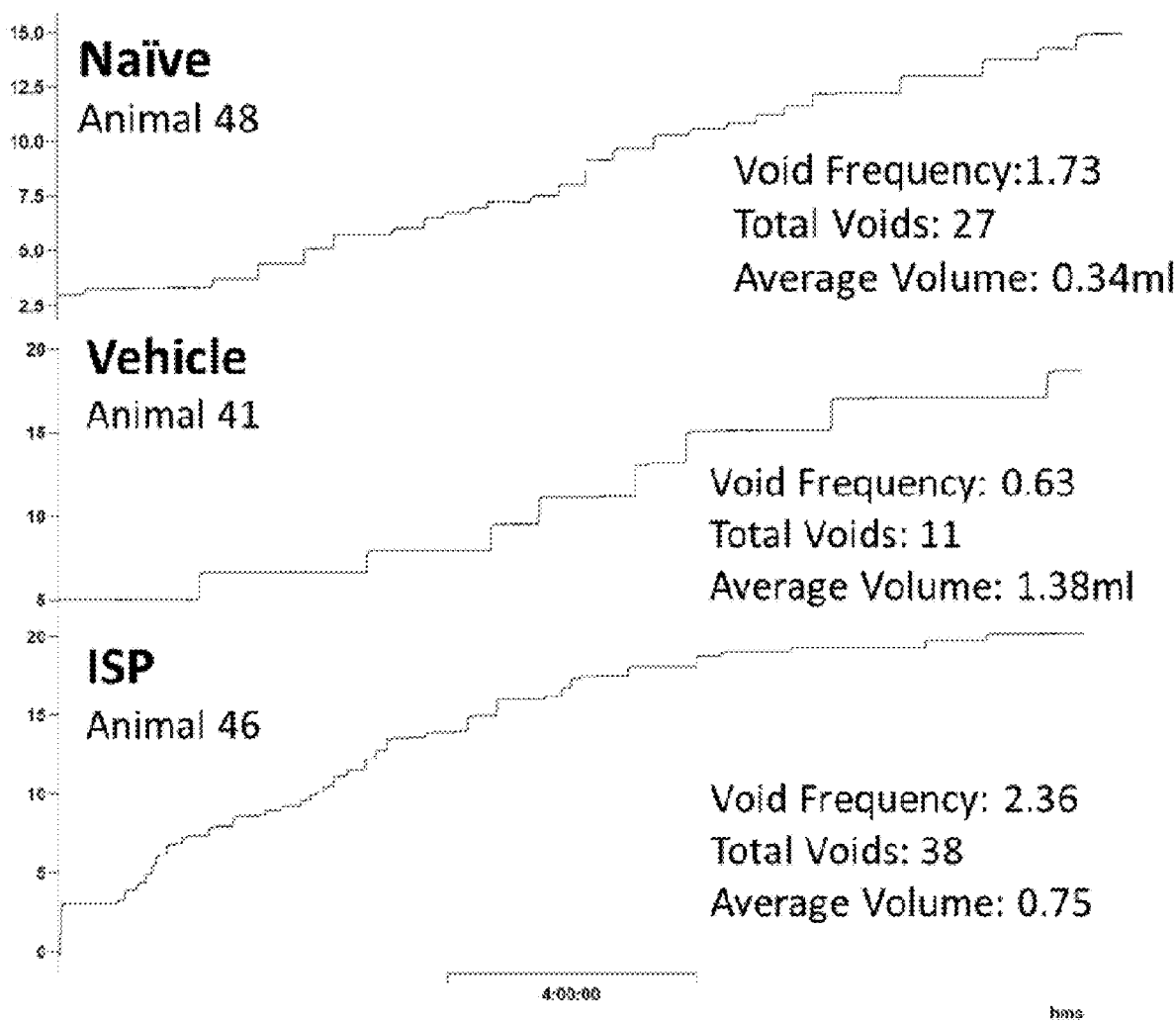
FIG. 12 illustrates a graph showing urinary frequency and volume of vehicle treated SCI animals and ISP treated SCI animals.

Recovery of urinary behavior was measured with metabolic cages. Animals were placed in metabolic cages for a dark cycle at 4, 8 and 12 weeks post injury where urinations were measured via a force transducer. FIG. 12 shows that while no significant recovery was seen on average at 4 or 8 weeks, ISP led to a significant increase in void frequency at 12 weeks post injury. While naïve animals urinate twice per hour on average, vehicle treated and ILP treated animals have significantly decreased frequency, once every two hours, with significantly increased volume/void. ISP treatment significantly increased the post-injury void frequency by two fold on average, with multiple animals reaching normal (naïve) micturition frequency levels.

To test whether animals had full control of bladder muscles and sphincter muscle contractility, animals underwent terminal urodynamic analyses at 14 weeks post injury. Under urodynamics and slow perfusion of saline into the bladder, naïve animals contract their bladder muscles leading to a sharp increase in pressure in the bladder (top trace). The drop in pressure corresponds to bursting of the external urethral sphincter, which helps expel urine from the animals. Both of these behaviors are completely lost following spinal cord injury, where the gradual rise in pressure in the bladder eventually leads to a maximum being reached and saline leaking out. The external urethral sphincter occasionally bursts, but doesn't correlate with bladder detrouser contractions leading to improper voiding of urine (detrouser sphincter dyssenergia). FIGS. 13(A-B) show that following ISP treatment, many animals recovered coordinated bladder contractions with patterned external urethral sphincter bursting (marked by red arrows).

Recovery beyond that of vehicle treated animals was defined as being greater than two standard deviations better than vehicle mean (micturition and BBB). Animals were placed into each group. 13 of 15 animals showed significant behavioral improvements, with 4 animals regaining significant function in all three behaviors.

Example 8

This Example shows 5HT expression of vehicle treated SCI animals and the ISP peptide treated SCI animals.

Methods

Animals were transcardially perfused with 4% paraformaldeyhde and the spinal column was dissected. Following an additional day in PFA, spinal cords were dissected out and cryoprotected for 3-7 days in 30% sucrose. The segment corresponding to L1-L3 was embedded and 20 µM transverse sections were placed onto slides.

Slides were blocked with 5% goat serum and probed with a primary antibody to 5HT (1:500, Immunostar). Following a wash and incubation with the appropriate secondary antibody, the slides were coverslipped and sealed. Images were taken on a florescent microscope at 2× under identical exposure, gain, gamma and offset to make comparisons between slides.

For axonal density analysis, the gray matter was outlined and mean pixel intensity was calculated in ImageJ. Since minimal staining was seen in the dorsal columns, the pixel intensity of this region was subtracted as an internal background of each individual section. One section selected randomly every 200 µm was analyzed over a total distance of 2 cm (10 segments). The highest and lowest pixel intensity was removed, with the remaining 8 averaged.

Results

Figure 14:
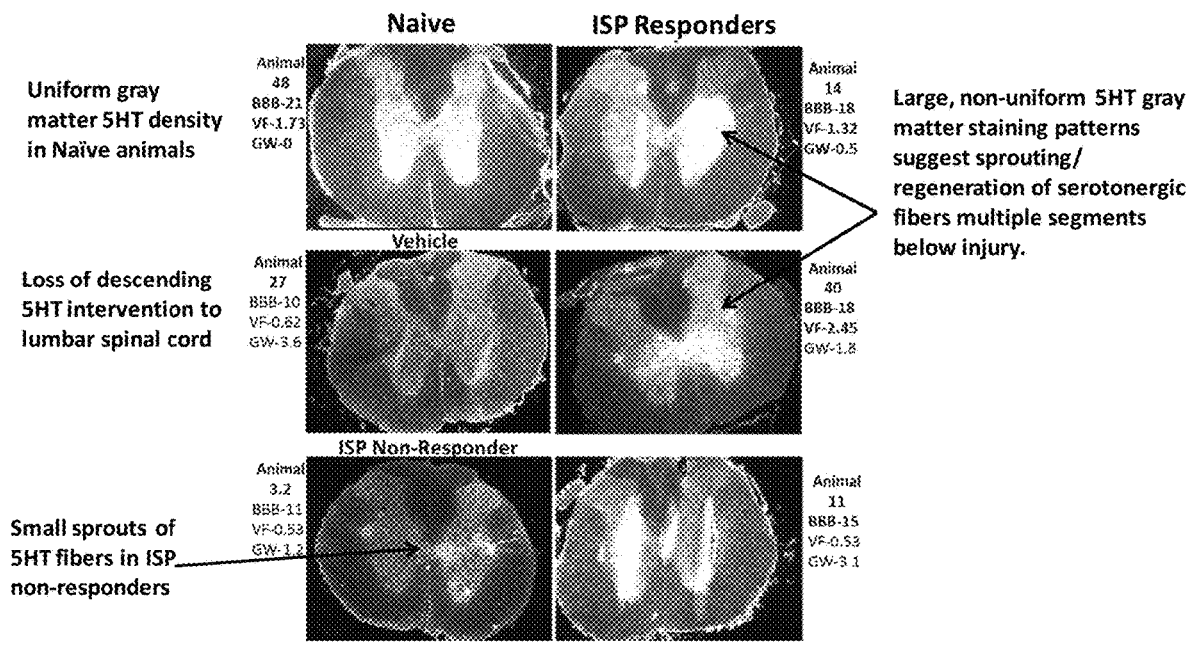
FIG. 14 illustrates photographs showing 5HT expression (axonal density) in lumbar spinal cord of vehicle treated SCI animals and ISP treated SCI animals.
Figure 15:
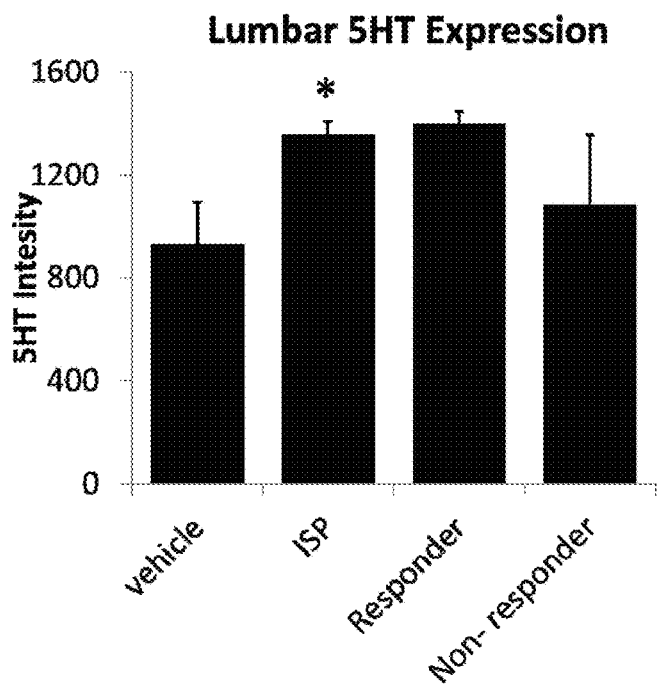
FIG. 15 illustrates a graph showing lumbar 5HT expression of vehicle treated SCI animals and ISP treated SCI animals.

5HT is a critical neurotransmitter in the spinal cord whose role is controlling the gain and excitability of motor networks. When combined with other treatments, 5HT agonists can significantly increase motor behaviors following spinal cord injury. We stained for 5HT expression in the lumbar spinal cord, multiple segments below the level of injury. The lumbar spinal cord contains the pacemakers for hind-limb locomotion and bladder control and contains the motor neurons for the legs and bladder muscles. FIG. 14 shows that in naïve animals, 5HT expression, or axonal density, was very high, with uniform staining patterns in the left and right gray matter. At higher magnification, fibers can be seen penetrating the white matter. 14 weeks following spinal cord injury, the expression of 5HT is significantly lower in vehicle treated control animals, with only a few small patches remaining in the gray matter. ISP treatment led to a dramatic increase in 5HT staining throughout the gray matter. The staining was remarkably robust and varied greatly from section to section in discrete non-uniform patches throughout the gray matter. This pattern suggests sprouting and/or regeneration of 5HT to spared motor-output centers. The increase in 5HT expression correlated well with behavioral recovery, as the two ISP non-responders did not show a dramatic rise in 5HT expression. Quantification showed again that 5HT expression throughout the gray matter was significantly increased (FIG. 15).

Example 9

Several proteins and pathways were identified that act downstream of the LAR family outside of phosphatase activity (FIG. 4). Of these, Caskin (Ckn) and LAR-interacting protein α (Liprin-α) have critical roles in both synapse formation and axonal guidance. mCkn1 directly binds mLAR and mPTPRδ, and mCkn2 directly binds mLAR and mPTPσ in a yeast two hybrid interaction system. Ckn's interaction with LAR family phosphatases was mapped to a region containing two sterile-alpha motifs (SAM domains) domain account for the phenotype. We created a homology map for drosophila, mouse, rat, and human Ckn family members using BLAST to align protein accession sequences as shown in Table 3.

Table 3 shows the first SAM domain is conserved between Ckn family members. We designed a 20-amino acid peptide that we hypothesize that acts as a small molecule competitor to LAR family phosphatase/Ckn binding, and mitigate downstream LAR family signaling. Work in the drosophila system identifies the C-terminal region of dCkn as necessary for downstream signaling events. We designed 20-amino acid peptides for both mCkn1 and mCkn2 that can potentially act as small molecule competitors to downstream targets, albeit these targets.

TABLE 3

Caskin1 C-Terminus Alignment

| | | | | |
|---|---|---|---|---|
| dCkn | 888 | VSVNVLNDIGNMANLTDELDAMLEEEKRV | 917 | SEQ ID NO: 75 |
| mCkn1 | 1376 | STGSILEDIGSMFDDLADQLDAMLE | 1400 | SEQ ID NO: 76 |
| rCkn1 | 1406 | STGSILEDIGSMFDDLADQLDAMLE | 1430 | SEQ ID NO: 77 |
| hCkn1 | 1325 | STGSILEDIGSMFDDLADQLDAMLE | 1349 | SEQ ID NO: 39 |

Caskin2 C-Terminus Alignment

| | | | | |
|---|---|---|---|---|
| dCkn | 888 | VSVNVLNDIGNMANLTDELDAMLEEEKRV | 317 | SEQ ID NO: 78 |
| mCkn2 | 1177 | STKHILDDISTMFDALADQLDAMLD | 1201 | SEQ ID NO: 79 |
| rCkn2 | 1176 | STKHILDDISTMFDALADQLDAMLD | 1200 | SEQ ID NO: 80 |
| hCkn2 | 1178 | STKHILDDISTMFDALADQLDAMLD | 1202 | SEQ ID NO: 40 |

Caskin SAM Domain alignment

| | | | | |
|---|---|---|---|---|
| dCkn | 284 | PTIARMTPEDLTAIGIKNPHHRERIKQRID | 313 | SEQ ID NO: 81 |
| mCkn1 | 519 | PTISRMTPEDLTAIGVTKPGHRKKITAEIS | 548 | SEQ ID NO: 82 |
| mCkn2 | 517 | PTISRMTPEDLTAIGVTKPGHRKKIASEIA | 546 | SEQ ID NO: 83 |
| rCkn1 | 503 | PTISRMTPEDLTAIGVTKPGHRKKITAEIS | 532 | SEQ ID NO: 84 |
| rCkn2 | 517 | PTISRMTPEDLTAIGVTKPGHRKKIASEIA | 546 | SEQ ID NO: 85 |
| hCkn1 | 419 | PTISRMTPEDLTAIGVTKPGHRKKIAAEIS | 448 | SEQ ID NO: 38 |
| hCkn2 | 518 | PTISRMTPEDLTAIGVTKPGHRKKIASEIA | 547 | SEQ ID NO: 86 |

Downstream Function Blocking Peptides

| | | |
|---|---|---|
| TAT-Caskin1/2_SAM | NH$_2$-GRKKRRQRRRCMTPEDLTAIGVTKPGHRKKI-NH$_2$ | SEQ ID NO: 71 |
| TAT-Caskin1_C | NH$_2$-GRKKRRQRRRCLEDIGSMFDDLADQLDAMLE | SEQ ID NO: 72 |
| TAT-Caskin2_C | NH$_2$-GRKKRRQRRRCLDDISTMFDALADQLDAMLD | SEQ ID NO: 73 |

Liprin family members play critical roles in the development and maintenance of synapses (We hypothesize that Liprin-α may act in signal transduction downstream of LAR phosphatases. Yeast-2-hybrid interaction screening implicates the first SAM domain of Liprin-α family members as the binding region for LAR phosphatase family members. We designed a 20-amino acid peptide that corresponds to an identical region within the first SAM domain of all 4 Liprin-α family members (Table 4). It is interesting that the 4 orthologs of Liprin-α retain this identical region through evolution, implicating this region as functionally important. We hypothesize that this small molecule competitor can be used to disrupt LAR-Liprin-α$_{1-4}$ interactions, disrupting downstream signaling of LAR phosphatase family members.

TABLE 4

Liprin alpha SAM alignment

| | | | | |
|---|---|---|---|---|
| mLα1 | 921 | WLELWGMPAWYVAACRANVKSGAIMSALSD | 950 | SEQ ID NO: 41 |
| mLα2 | 906 | WLELWGMPAWYVAACRANVKSGAIMSALSD | 935 | SEQ ID NO: 87 |
| mLα3 | 898 | WLELWGMPAWYVAACRANVKSGAIMANLSD | 927 | SEQ ID NO: 88 |
| mLα4 | 803 | WLELWGMPAWYVAACRANVKSGAIMSALSD | 833 | SEQ ID NO: 89 |
| rLα1 | 666 | WLELWGMPAWYVAACRANVKSGAIMSALSD | 695 | SEQ ID NO: 90 |

TABLE 4-continued

| | | | | | |
|---|---|---|---|---|---|
| rLα2 | 907 | WLELWGMPAWYVAACRANVKSGAIMSALSD | 936 | SEQ ID NO: 91 | |
| rLα3 | 896 | WLELWGMPAWYVAACRANVKSGAIMANLSD | 925 | SEQ ID NO: 92 | |
| rLα4 | 697 | WLELWGMPAWYVAACRANVKSGAIMSALSD | 726 | SEQ ID NO: 93 | |

Downstream Function Blocking Peptides

| | | |
|---|---|---|
| TAT-Liprin alpha 1 | NH$_2$-GRKKRRQRRRCGMPAWYVAACRANVKSGAIM-NH$_2$ | SEQ ID NO: 74 |

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, we claim:

1. A composition comprising:
a peptide comprising an amino acid sequence with at least 70% identity to SEQ ID NO:37 and a transport moiety linked to the peptide and which facilitates uptake of the peptide by a cell.

2. The composition of claim 1, wherein the amino acid sequence has at least 75% identity to SEQ ID NO:37.

3. The composition of claim 1, wherein the amino acid sequence has at least 80% identity to SEQ ID NO:37.

4. The composition of claim 1, wherein the amino acid sequence has at least at least 85% identity to SEQ ID NO:37.

5. The composition of claim 1, wherein the amino acid sequence has at least at least 90% identity or at least 95% to SEQ ID NO:37.

6. The composition of claim 1, wherein the peptide comprises a substitution of an amino acid of at least one of residue 4, 5, 6, 7, 9, 10, 12, or 13 of SEQ ID NO: 37 for another amino acid, wherein the amino acid residue 4E is substituted with D or Q, amino acid residue 5R is substituted with H, L or K, amino acid residue 6L is substituted with I, V or M, amino acid residue 7K is substituted with R or H, amino acid residue 9N is substituted with E or D, amino acid residue 10D is substituted with E or N, amino acid residue 12L is substituted with I, V or M, and/or amino acid residue 13K is substituted with R or H.

7. The composition of claim 1, wherein the peptide comprises an amino acid sequence selected from the group consisting of SEQ ID NOs:9-33 and 37.

8. The composition of claim 1, wherein the transport moiety is an HIV Tat transport moiety.

9. The composition of claim 1, wherein the transport moiety is linked to the peptide by a peptide linker.

10. The composition of claim 1, wherein the agent comprises an amino acid sequence selected from the group consisting of SEQ ID NOs:42-66 and 70.

11. The composition of claim 1, wherein the peptide inhibits one or more of catalytic activity, signaling, or function of protein tyrosine phosphatase sigma (PTPσ).

12. A method of inhibiting one or more of catalytic activity, signaling, and/or function of receptor protein tyrosine phosphatase sigma (PTPσ), comprising contacting the cell with an effective amount of the composition of claim 1.

13. The method of claim 12, wherein the amino acid sequence has at least 75%, at least 80%, at least 85%, at least 90%, or at least 95% identity to SEQ ID NO:37.

14. The method of claim 12, wherein the peptide comprises a substitution of an amino acid of at least one of residue 4, 5, 6, 7, 9, 10, 12, or 13 of SEQ ID NO: 37 for another amino acid, wherein the amino acid residue 4E is substituted with D or Q, amino acid residue 5R is substituted with H, L or K, amino acid residue 6L is substituted with I, V or M, amino acid residue 7K is substituted with R or H, amino acid residue 9N is substituted with E or D, amino acid residue 10D is substituted with E or N, amino acid residue 12L is substituted with I, V or M, and/or amino acid residue 13K is substituted with R or H.

15. The method of claim 12, wherein the peptide comprises an amino acid sequence selected from the group consisting of SEQ ID NOs:9-33 and 37.

16. The method of claim 12, wherein the transport moiety is an HIV Tat transport moiety.

17. The method of claim 12, wherein the transport moiety is linked to the peptide by a peptide linker.

18. The method of claim 12, wherein the agent comprises an amino acid sequence selected from the group consisting of SEQ ID NOs:42-66 and 70.

19. The method of claim 12, wherein the cell is in a subject, and contacting the cell comprises administering to the subject an effective amount of the composition.

20. The method of claim 19, wherein the composition is administered systemically to the subject.

* * * * *

SEQUENCE LISTING

<160> NUMBER OF SEQ ID NOS: 96

<210> SEQ ID NO 1
<211> LENGTH: 33
<212> TYPE: PRT
<213> ORGANISM: Mus musculus

<400> SEQUENCE: 1

Pro Ile Pro Ile Thr Asp Leu Ala Asp Asn Ile Glu Arg Leu Lys Ala
1               5                   10                  15

Asn Asp Gly Lys Leu Phe Ser Gln Glu Tyr Glu Ser Ile Asp Pro Gly
            20                  25                  30

Gln

<210> SEQ ID NO 2
<211> LENGTH: 33
<212> TYPE: PRT
<213> ORGANISM: Rat coronavirus

<400> SEQUENCE: 2

Pro Ile Pro Ile Thr Asp Leu Ala Asp Asn Ile Glu Arg Leu Lys Ala
1               5                   10                  15

Asn Asp Gly Lys Leu Phe Ser Gln Glu Tyr Glu Ser Ile Asp Pro Gly
            20                  25                  30

Gln

<210> SEQ ID NO 3
<211> LENGTH: 33
<212> TYPE: PRT
<213> ORGANISM: Homo sapiens

<400> SEQUENCE: 3

Pro Ile Pro Ile Thr Asp Leu Ala Asp Asn Ile Glu Arg Leu Lys Ala
1               5                   10                  15

Asn Asp Gly Lys Leu Phe Ser Gln Glu Tyr Glu Ser Ile Asp Pro Gly
            20                  25                  30

Gln

<210> SEQ ID NO 4
<211> LENGTH: 33
<212> TYPE: PRT

-continued

<213> ORGANISM: Mus musculus

<400> SEQUENCE: 4

Pro Ile Pro Ile Thr Asp Met Ala Glu His Met Glu Arg Leu Lys Ala
1               5                   10                  15

Asn Asp Ser Leu Lys Leu Ser Gln Glu Tyr Glu Ser Ile Asp Pro Gly
            20                  25                  30

Gln

<210> SEQ ID NO 5
<211> LENGTH: 33
<212> TYPE: PRT
<213> ORGANISM: Rat coronavirus

<400> SEQUENCE: 5

Pro Ile Pro Ile Thr Asp Met Ala Glu His Met Glu Arg Leu Lys Ala
1               5                   10                  15

Asn Asp Ser Leu Lys Leu Ser Gln Glu Tyr Glu Ser Ile Asp Pro Gly
            20                  25                  30

Gln

<210> SEQ ID NO 6
<211> LENGTH: 33
<212> TYPE: PRT
<213> ORGANISM: Homo sapiens

<400> SEQUENCE: 6

Pro Ile Pro Ile Ala Asp Met Ala Glu His Thr Glu Arg Leu Lys Ala
1               5                   10                  15

Asn Asp Ser Leu Lys Leu Ser Gln Glu Tyr Glu Ser Ile Asp Pro Gly
            20                  25                  30

Gln

<210> SEQ ID NO 7
<211> LENGTH: 33
<212> TYPE: PRT
<213> ORGANISM: Mus musculus

<400> SEQUENCE: 7

Pro Ile Pro Ile Leu Glu Leu Ala Asp His Ile Glu Arg Leu Lys Ala
1               5                   10                  15

Asn Asp Asn Leu Lys Phe Ser Gln Glu Tyr Glu Ser Ile Asp Pro Gly
            20                  25                  30

Gln

<210> SEQ ID NO 8
<211> LENGTH: 33
<212> TYPE: PRT
<213> ORGANISM: Homo sapiens

<400> SEQUENCE: 8

Pro Ile Pro Ile Leu Glu Leu Ala Asp His Ile Glu Arg Leu Lys Ala
1               5                   10                  15

Asn Asp Asn Leu Lys Phe Ser Gln Glu Tyr Glu Ser Ile Asp Pro Gly
            20                  25                  30

Gln

<210> SEQ ID NO 9
<211> LENGTH: 22

```
<212> TYPE: PRT
<213> ORGANISM: Xenopus borealis

<400> SEQUENCE: 9

Asp Leu Ala Glu His Thr Glu His Leu Lys Ala Asn Asp Asn Leu Lys
1               5                   10                  15

Ser Gln Glu Tyr Glu Ser
            20

<210> SEQ ID NO 10
<211> LENGTH: 21
<212> TYPE: PRT
<213> ORGANISM: Anolis carolinensis

<400> SEQUENCE: 10

Asp His Thr Glu His Leu Lys Ala Asn Asp Asn Leu Lys Leu Ser Gln
1               5                   10                  15

Glu Tyr Glu Ser Ile
            20

<210> SEQ ID NO 11
<211> LENGTH: 24
<212> TYPE: PRT
<213> ORGANISM: Danio rerio

<400> SEQUENCE: 11

Glu Leu Ala Glu His Thr Glu Leu Leu Lys Ala Asn Asp Asn Leu Lys
1               5                   10                  15

Leu Ser Gln Glu Tyr Glu Ser Ile
            20

<210> SEQ ID NO 12
<211> LENGTH: 24
<212> TYPE: PRT
<213> ORGANISM: Oreochromis aureus

<400> SEQUENCE: 12

Glu Leu Ala Glu His Thr Glu Leu Leu Lys Ala Asn Asp Asn Leu Lys
1               5                   10                  15

Leu Ser Gln Glu Tyr Glu Ser Ile
            20

<210> SEQ ID NO 13
<211> LENGTH: 24
<212> TYPE: PRT
<213> ORGANISM: Gallus gallus

<400> SEQUENCE: 13

Glu Leu Ala Glu His Thr Glu His Leu Lys Ala Asn Asp Asn Leu Lys
1               5                   10                  15

Leu Ser Gln Glu Tyr Glu Ser Ile
            20

<210> SEQ ID NO 14
<211> LENGTH: 24
<212> TYPE: PRT
<213> ORGANISM: Fringilla coelebs

<400> SEQUENCE: 14

Glu Leu Ala Glu His Thr Glu His Leu Lys Ala Asn Asp Asn Leu Lys
1               5                   10                  15

Leu Ser Gln Glu Tyr Glu Ser Ile
```

```
<210> SEQ ID NO 15
<211> LENGTH: 24
<212> TYPE: PRT
<213> ORGANISM: Ornithorhynchus anatinus

<400> SEQUENCE: 15

Glu Leu Ala Glu His Thr Asp His Leu Lys Ala Asn Asp Asn Leu Lys
1               5                   10                  15

Leu Ser Gln Glu Tyr Glu Ser Ile
            20

<210> SEQ ID NO 16
<211> LENGTH: 24
<212> TYPE: PRT
<213> ORGANISM: Sarcophilus harrisii

<400> SEQUENCE: 16

Glu Met Ala Glu His Thr Glu His Leu Lys Ala Asn Asp Asn Leu Lys
1               5                   10                  15

Leu Ser Gln Glu Tyr Glu Ser Ile
            20

<210> SEQ ID NO 17
<211> LENGTH: 24
<212> TYPE: PRT
<213> ORGANISM: Mustela putorius

<400> SEQUENCE: 17

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 18
<211> LENGTH: 24
<212> TYPE: PRT
<213> ORGANISM: Galago alleni

<400> SEQUENCE: 18

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 19
<211> LENGTH: 24
<212> TYPE: PRT
<213> ORGANISM: Callithrix aurita

<400> SEQUENCE: 19

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 20
<211> LENGTH: 24
<212> TYPE: PRT
<213> ORGANISM: Rattus rattus

<400> SEQUENCE: 20
```

Asp Met Ala Glu His Met Glu Arg Leu Lys Ala Asn Asp Ser Leu Lys
1               5                   10                  15

Leu Ser Gln Glu Tyr Glu Ser Ile
            20

<210> SEQ ID NO 21
<211> LENGTH: 24
<212> TYPE: PRT
<213> ORGANISM: Mus musculus

<400> SEQUENCE: 21

Asp Met Ala Glu His Met Glu Arg Leu Lys Ala Asn Asp Ser Leu Lys
1               5                   10                  15

Leu Ser Gln Glu Tyr Glu Ser Ile
            20

<210> SEQ ID NO 22
<211> LENGTH: 24
<212> TYPE: PRT
<213> ORGANISM: Canis familiaris

<400> SEQUENCE: 22

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 23
<211> LENGTH: 24
<212> TYPE: PRT
<213> ORGANISM: Sus barbatus

<400> SEQUENCE: 23

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 24
<211> LENGTH: 24
<212> TYPE: PRT
<213> ORGANISM: Bos primigenius

<400> SEQUENCE: 24

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 25
<211> LENGTH: 24
<212> TYPE: PRT
<213> ORGANISM: Ovis aries

<400> SEQUENCE: 25

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 26

-continued

```
<211> LENGTH: 24
<212> TYPE: PRT
<213> ORGANISM: Orcinus orca

<400> SEQUENCE: 26

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 27
<211> LENGTH: 24
<212> TYPE: PRT
<213> ORGANISM: Saimiri sciureus

<400> SEQUENCE: 27

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 28
<211> LENGTH: 24
<212> TYPE: PRT
<213> ORGANISM: Papio hamadryas

<400> SEQUENCE: 28

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 29
<211> LENGTH: 24
<212> TYPE: PRT
<213> ORGANISM: Primate calicivirus

<400> SEQUENCE: 29

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 30
<211> LENGTH: 24
<212> TYPE: PRT
<213> ORGANISM: Primate calicivirus

<400> SEQUENCE: 30

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 31
<211> LENGTH: 24
<212> TYPE: PRT
<213> ORGANISM: Macaca radiata

<400> SEQUENCE: 31

Asp Met Ala Glu His Thr Glu Arg Leu Lys Ala Asn Asp Ser Leu Lys
1               5                   10                  15
```

Leu Ser Gln Glu Tyr Glu Ser Ile
            20

<210> SEQ ID NO 32
<211> LENGTH: 24
<212> TYPE: PRT
<213> ORGANISM: Pan troglodytes

<400> SEQUENCE: 32

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 33
<211> LENGTH: 24
<212> TYPE: PRT
<213> ORGANISM: Homo sapiens

<400> SEQUENCE: 33

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 34
<211> LENGTH: 24
<212> TYPE: PRT
<213> ORGANISM: Rattus rattus

<400> SEQUENCE: 34

Asp Leu Ala Asp Asn Ile Glu Arg Leu Lys Ala Asn Asp Gly Leu Lys
1               5                   10                  15

Phe Ser Gln Glu Tyr Glu Ser Ile
            20

<210> SEQ ID NO 35
<211> LENGTH: 24
<212> TYPE: PRT
<213> ORGANISM: Rattus rattus

<400> SEQUENCE: 35

Glu Leu Ala Asp His Ile Glu Arg Leu Lys Ala Asn Asp Asn Leu Lys
1               5                   10                  15

Phe Ser Gln Glu Tyr Glu Ser Ile
            20

<210> SEQ ID NO 36
<211> LENGTH: 24
<212> TYPE: PRT
<213> ORGANISM: Rattus rattus

<400> SEQUENCE: 36

Lys Leu Glu Glu Glu Ile Asn Arg Arg Met Ala Asp Asp Asn Lys Ile
1               5                   10                  15

Phe Arg Glu Glu Phe Asn Ala Leu
            20

<210> SEQ ID NO 37
<211> LENGTH: 14
<212> TYPE: PRT
<213> ORGANISM: Artificial Sequence
<220> FEATURE:

<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Thr or Met

<400> SEQUENCE: 37

```
Glu His Xaa Glu Arg Leu Lys Ala Asn Asp Ser Leu Lys Leu
1               5                   10
```

<210> SEQ ID NO 38
<211> LENGTH: 30
<212> TYPE: PRT
<213> ORGANISM: Homo sapiens

<400> SEQUENCE: 38

```
Pro Thr Ile Ser Arg Met Thr Pro Glu Asp Leu Thr Ala Ile Gly Val
1               5                   10                  15

Thr Lys Pro Gly His Arg Lys Lys Ile Ala Ala Glu Ile Ser
            20                  25                  30
```

<210> SEQ ID NO 39
<211> LENGTH: 25
<212> TYPE: PRT
<213> ORGANISM: Homo sapiens

<400> SEQUENCE: 39

```
Ser Thr Gly Ser Ile Leu Glu Asp Ile Gly Ser Met Phe Asp Asp Leu
1               5                   10                  15

Ala Asp Gln Leu Asp Ala Met Leu Glu
            20                  25
```

<210> SEQ ID NO 40
<211> LENGTH: 45
<212> TYPE: PRT
<213> ORGANISM: Homo sapiens

<400> SEQUENCE: 40

```
Ser Thr Lys His Ile Leu Asp Asp Ile Ser Thr Met Phe Asp Ala Leu
1               5                   10                  15

Ala Asp Gln Leu Asp Ala Met Leu Asp Leu Asp Asp Ile Ser Thr Met
            20                  25                  30

Phe Asp Ala Leu Ala Asp Gln Leu Asp Ala Met Leu Asp
        35                  40                  45
```

<210> SEQ ID NO 41
<211> LENGTH: 30
<212> TYPE: PRT
<213> ORGANISM: Homo sapiens

<400> SEQUENCE: 41

```
Trp Leu Glu Leu Trp Gly Met Pro Ala Trp Tyr Val Ala Ala Cys Arg
1               5                   10                  15

Ala Asn Val Lys Ser Gly Ala Ile Met Ser Ala Leu Ser Asp
            20                  25                  30
```

<210> SEQ ID NO 42
<211> LENGTH: 33
<212> TYPE: PRT
<213> ORGANISM: Xenopus borealis

<400> SEQUENCE: 42

```
Gly Arg Lys Lys Arg Arg Gln Arg Arg Arg Cys Asp Leu Ala Glu His
```

```
1               5                   10                  15
Thr Glu His Leu Lys Ala Asn Asp Asn Leu Lys Ser Gln Glu Tyr Glu
            20                  25                  30
Ser
```

<210> SEQ ID NO 43
<211> LENGTH: 32
<212> TYPE: PRT
<213> ORGANISM: Anolis carolinensis

<400> SEQUENCE: 43

```
Gly Arg Lys Lys Arg Arg Gln Arg Arg Cys Asp His Thr Glu His
1               5                   10                  15
Leu Lys Ala Asn Asp Asn Leu Lys Leu Ser Gln Glu Tyr Glu Ser Ile
            20                  25                  30
```

<210> SEQ ID NO 44
<211> LENGTH: 35
<212> TYPE: PRT
<213> ORGANISM: Danio rerio

<400> SEQUENCE: 44

```
Gly Arg Lys Lys Arg Arg Gln Arg Arg Cys Glu Leu Ala Glu His
1               5                   10                  15
Thr Glu Leu Leu Lys Ala Asn Asp Asn Leu Lys Leu Ser Gln Glu Tyr
            20                  25                  30
Glu Ser Ile
        35
```

<210> SEQ ID NO 45
<211> LENGTH: 35
<212> TYPE: PRT
<213> ORGANISM: Tilapia nilotica

<400> SEQUENCE: 45

```
Gly Arg Lys Lys Arg Arg Gln Arg Arg Cys Glu Leu Ala Glu His
1               5                   10                  15
Thr Glu Leu Leu Lys Ala Asn Asp Asn Leu Lys Leu Ser Gln Glu Tyr
            20                  25                  30
Glu Ser Ile
        35
```

<210> SEQ ID NO 46
<211> LENGTH: 35
<212> TYPE: PRT
<213> ORGANISM: Gallus gallus

<400> SEQUENCE: 46

```
Gly Arg Lys Lys Arg Arg Gln Arg Arg Cys Glu Leu Ala Glu His
1               5                   10                  15
Thr Glu His Leu Lys Ala Asn Asp Asn Leu Lys Leu Ser Gln Glu Tyr
            20                  25                  30
Glu Ser Ile
        35
```

<210> SEQ ID NO 47
<211> LENGTH: 35
<212> TYPE: PRT
<213> ORGANISM: Fringilla coelebs

<400> SEQUENCE: 47

-continued

```
Gly Arg Lys Lys Arg Arg Gln Arg Arg Cys Glu Leu Ala Glu His
1               5                   10                  15

Thr Glu His Leu Lys Ala Asn Asp Asn Leu Lys Leu Ser Gln Glu Tyr
            20                  25                  30

Glu Ser Ile
        35

<210> SEQ ID NO 48
<211> LENGTH: 35
<212> TYPE: PRT
<213> ORGANISM: Ornithorhynchus anatinus

<400> SEQUENCE: 48

Gly Arg Lys Lys Arg Arg Gln Arg Arg Cys Glu Leu Ala Glu His
1               5                   10                  15

Thr Asp His Leu Lys Ala Asn Asp Asn Leu Lys Leu Ser Gln Glu Tyr
            20                  25                  30

Glu Ser Ile
        35

<210> SEQ ID NO 49
<211> LENGTH: 35
<212> TYPE: PRT
<213> ORGANISM: Sarcophilus harrisii

<400> SEQUENCE: 49

Gly Arg Lys Lys Arg Arg Gln Arg Arg Cys Glu Met Ala Glu His
1               5                   10                  15

Thr Glu His Leu Lys Ala Asn Asp Asn Leu Lys Leu Ser Gln Glu Tyr
            20                  25                  30

Glu Ser Ile
        35

<210> SEQ ID NO 50
<211> LENGTH: 35
<212> TYPE: PRT
<213> ORGANISM: Mustela putorius

<400> SEQUENCE: 50

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 51
<211> LENGTH: 35
<212> TYPE: PRT
<213> ORGANISM: Galago alleni

<400> SEQUENCE: 51

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35
```

<210> SEQ ID NO 52
<211> LENGTH: 35
<212> TYPE: PRT
<213> ORGANISM: Callithrix argentata

<400> SEQUENCE: 52

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 53
<211> LENGTH: 35
<212> TYPE: PRT
<213> ORGANISM: Rattus rattus

<400> SEQUENCE: 53

Gly Arg Lys Lys Arg Arg Gln Arg Arg Cys Asp Met Ala Glu His
1               5                   10                  15

Met Glu Arg Leu Lys Ala Asn Asp Ser Leu Lys Leu Ser Gln Glu Tyr
            20                  25                  30

Glu Ser Ile
        35

<210> SEQ ID NO 54
<211> LENGTH: 35
<212> TYPE: PRT
<213> ORGANISM: Mus musculus

<400> SEQUENCE: 54

Gly Arg Lys Lys Arg Arg Gln Arg Arg Cys Asp Met Ala Glu His
1               5                   10                  15

Met Glu Arg Leu Lys Ala Asn Asp Ser Leu Lys Leu Ser Gln Glu Tyr
            20                  25                  30

Glu Ser Ile
        35

<210> SEQ ID NO 55
<211> LENGTH: 35
<212> TYPE: PRT
<213> ORGANISM: Canis familiaris

<400> SEQUENCE: 55

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 56
<211> LENGTH: 35
<212> TYPE: PRT
<213> ORGANISM: Sus barbatus

<400> SEQUENCE: 56

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr

Glu Ser Ile
        35

<210> SEQ ID NO 57
<211> LENGTH: 35
<212> TYPE: PRT
<213> ORGANISM: Bos primigenius

<400> SEQUENCE: 57

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 58
<211> LENGTH: 35
<212> TYPE: PRT
<213> ORGANISM: Ovis aries

<400> SEQUENCE: 58

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 59
<211> LENGTH: 35
<212> TYPE: PRT
<213> ORGANISM: Orcinus orca

<400> SEQUENCE: 59

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 60
<211> LENGTH: 35
<212> TYPE: PRT
<213> ORGANISM: Saimiri boliviensis

<400> SEQUENCE: 60

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 61
<211> LENGTH: 35
<212> TYPE: PRT
<213> ORGANISM: Papio hamadryas

```
<400> SEQUENCE: 61

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 62
<211> LENGTH: 35
<212> TYPE: PRT
<213> ORGANISM: Primate calicivirus

<400> SEQUENCE: 62

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 63
<211> LENGTH: 35
<212> TYPE: PRT
<213> ORGANISM: Primate calicivirus

<400> SEQUENCE: 63

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 64
<211> LENGTH: 35
<212> TYPE: PRT
<213> ORGANISM: Macaca arctoides

<400> SEQUENCE: 64

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 65
<211> LENGTH: 35
<212> TYPE: PRT
<213> ORGANISM: Pan troglodytes

<400> SEQUENCE: 65

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35
```

<210> SEQ ID NO 66
<211> LENGTH: 35
<212> TYPE: PRT
<213> ORGANISM: Homo sapiens

<400> SEQUENCE: 66

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 67
<211> LENGTH: 10
<212> TYPE: PRT
<213> ORGANISM: Homo sapiens

<400> SEQUENCE: 67

Asp Met Ala Glu His Thr Glu Arg Leu Lys
1               5                   10

<210> SEQ ID NO 68
<211> LENGTH: 4
<212> TYPE: PRT
<213> ORGANISM: Homo sapiens

<400> SEQUENCE: 68

Ala Asn Asp Ser
1

<210> SEQ ID NO 69
<211> LENGTH: 10
<212> TYPE: PRT
<213> ORGANISM: Homo sapiens

<400> SEQUENCE: 69

Leu Lys Leu Ser Gln Glu Tyr Glu Ser Ile
1               5                   10

<210> SEQ ID NO 70
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (14)..(14)
<223> OTHER INFORMATION: Xaa is Thr or Met

<400> SEQUENCE: 70

Gly Arg Lys Lys Arg Arg Gln Arg Arg Cys Glu His Xaa Glu Arg
1               5                   10                  15

Leu Lys Ala Asn Asp Ser Leu Lys Leu
            20                  25

<210> SEQ ID NO 71
<211> LENGTH: 31
<212> TYPE: PRT
<213> ORGANISM: Homo sapiens

<400> SEQUENCE: 71

Gly Arg Lys Lys Arg Arg Gln Arg Arg Cys Met Thr Pro Glu Asp

```
1               5                   10                  15
Leu Thr Ala Ile Gly Val Thr Lys Pro Gly His Arg Lys Lys Ile
                20                  25                  30
```

<210> SEQ ID NO 72
<211> LENGTH: 31
<212> TYPE: PRT
<213> ORGANISM: Homo sapiens

<400> SEQUENCE: 72

```
Gly Arg Lys Lys Arg Arg Gln Arg Arg Cys Leu Glu Asp Ile Gly
1               5                   10                  15
Ser Met Phe Asp Asp Leu Ala Asp Gln Leu Asp Ala Met Leu Glu
                20                  25                  30
```

<210> SEQ ID NO 73
<211> LENGTH: 31
<212> TYPE: PRT
<213> ORGANISM: Homo sapiens

<400> SEQUENCE: 73

```
Gly Arg Lys Lys Arg Arg Gln Arg Arg Cys Leu Asp Asp Ile Ser
1               5                   10                  15
Thr Met Phe Asp Ala Leu Ala Asp Gln Leu Asp Ala Met Leu Asp
                20                  25                  30
```

<210> SEQ ID NO 74
<211> LENGTH: 31
<212> TYPE: PRT
<213> ORGANISM: Homo sapiens

<400> SEQUENCE: 74

```
Gly Arg Lys Lys Arg Arg Gln Arg Arg Cys Gly Met Pro Ala Trp
1               5                   10                  15
Tyr Val Ala Ala Cys Arg Ala Asn Val Lys Ser Gly Ala Ile Met
                20                  25                  30
```

<210> SEQ ID NO 75
<211> LENGTH: 29
<212> TYPE: PRT
<213> ORGANISM: Homo sapiens

<400> SEQUENCE: 75

```
Val Ser Val Asn Val Leu Asn Asp Ile Gly Asn Met Ala Asn Leu Thr
1               5                   10                  15
Asp Glu Leu Asp Ala Met Leu Glu Glu Lys Arg Val
                20                  25
```

<210> SEQ ID NO 76
<211> LENGTH: 25
<212> TYPE: PRT
<213> ORGANISM: Mus musculus

<400> SEQUENCE: 76

```
Ser Thr Gly Ser Ile Leu Glu Asp Ile Gly Ser Met Phe Asp Asp Leu
1               5                   10                  15
Ala Asp Gln Leu Asp Ala Met Leu Glu
                20                  25
```

<210> SEQ ID NO 77
<211> LENGTH: 25
<212> TYPE: PRT

<213> ORGANISM: Rattus rattus

<400> SEQUENCE: 77

Ser Thr Gly Ser Ile Leu Glu Asp Ile Gly Ser Met Phe Asp Asp Leu
1               5                   10                  15
Ala Asp Gln Leu Asp Ala Met Leu Glu
            20                  25

<210> SEQ ID NO 78
<211> LENGTH: 29
<212> TYPE: PRT
<213> ORGANISM: Homo sapiens

<400> SEQUENCE: 78

Val Ser Val Asn Val Leu Asn Asp Ile Gly Asn Met Ala Asn Leu Thr
1               5                   10                  15
Asp Glu Leu Asp Ala Met Leu Glu Glu Glu Lys Arg Val
            20                  25

<210> SEQ ID NO 79
<211> LENGTH: 25
<212> TYPE: PRT
<213> ORGANISM: Mus musculus

<400> SEQUENCE: 79

Ser Thr Lys His Ile Leu Asp Asp Ile Ser Thr Met Phe Asp Ala Leu
1               5                   10                  15
Ala Asp Gln Leu Asp Ala Met Leu Asp
            20                  25

<210> SEQ ID NO 80
<211> LENGTH: 25
<212> TYPE: PRT
<213> ORGANISM: Rattus rattus

<400> SEQUENCE: 80

Ser Thr Lys His Ile Leu Asp Asp Ile Ser Thr Met Phe Asp Ala Leu
1               5                   10                  15
Ala Asp Gln Leu Asp Ala Met Leu Asp
            20                  25

<210> SEQ ID NO 81
<211> LENGTH: 30
<212> TYPE: PRT
<213> ORGANISM: Homo sapiens

<400> SEQUENCE: 81

Pro Thr Ile Ala Arg Met Thr Pro Glu Asp Leu Thr Ala Ile Gly Ile
1               5                   10                  15
Lys Asn Pro His His Arg Glu Arg Ile Lys Gln Arg Ile Asp
            20                  25                  30

<210> SEQ ID NO 82
<211> LENGTH: 30
<212> TYPE: PRT
<213> ORGANISM: Mus musculus

<400> SEQUENCE: 82

Pro Thr Ile Ser Arg Met Thr Pro Glu Asp Leu Thr Ala Ile Gly Val
1               5                   10                  15
Thr Lys Pro Gly His Arg Lys Lys Ile Thr Ala Glu Ile Ser
            20                  25                  30

<210> SEQ ID NO 83
<211> LENGTH: 30
<212> TYPE: PRT
<213> ORGANISM: Mus musculus

<400> SEQUENCE: 83

Pro Thr Ile Ser Arg Met Thr Pro Glu Asp Leu Thr Ala Ile Gly Val
1               5                   10                  15

Thr Lys Pro Gly His Arg Lys Lys Ile Ala Ser Glu Ile Ala
            20                  25                  30

<210> SEQ ID NO 84
<211> LENGTH: 30
<212> TYPE: PRT
<213> ORGANISM: Rattus rattus

<400> SEQUENCE: 84

Pro Thr Ile Ser Arg Met Thr Pro Glu Asp Leu Thr Ala Ile Gly Val
1               5                   10                  15

Thr Lys Pro Gly His Arg Lys Lys Ile Thr Ala Glu Ile Ser
            20                  25                  30

<210> SEQ ID NO 85
<211> LENGTH: 30
<212> TYPE: PRT
<213> ORGANISM: Rattus rattus

<400> SEQUENCE: 85

Pro Thr Ile Ser Arg Met Thr Pro Glu Asp Leu Thr Ala Ile Gly Val
1               5                   10                  15

Thr Lys Pro Gly His Arg Lys Lys Ile Ala Ser Glu Ile Ala
            20                  25                  30

<210> SEQ ID NO 86
<211> LENGTH: 30
<212> TYPE: PRT
<213> ORGANISM: Homo sapiens

<400> SEQUENCE: 86

Pro Thr Ile Ser Arg Met Thr Pro Glu Asp Leu Thr Ala Ile Gly Val
1               5                   10                  15

Thr Lys Pro Gly His Arg Lys Lys Ile Ala Ser Glu Ile Ala
            20                  25                  30

<210> SEQ ID NO 87
<211> LENGTH: 30
<212> TYPE: PRT
<213> ORGANISM: Mus musculus

<400> SEQUENCE: 87

Trp Leu Glu Leu Trp Gly Met Pro Ala Trp Tyr Val Ala Ala Cys Arg
1               5                   10                  15

Ala Asn Val Lys Ser Gly Ala Ile Met Ser Ala Leu Ser Asp
            20                  25                  30

<210> SEQ ID NO 88
<211> LENGTH: 30
<212> TYPE: PRT
<213> ORGANISM: Mus musculus

<400> SEQUENCE: 88

Trp Leu Glu Leu Trp Gly Met Pro Ala Trp Tyr Val Ala Ala Cys Arg
1               5                   10                  15

Ala Asn Val Lys Ser Gly Ala Ile Met Ala Asn Leu Ser Asp
            20                  25                  30

<210> SEQ ID NO 89
<211> LENGTH: 30
<212> TYPE: PRT
<213> ORGANISM: Mus musculus

<400> SEQUENCE: 89

Trp Leu Glu Leu Trp Gly Met Pro Ala Trp Tyr Val Ala Ala Cys Arg
1               5                   10                  15

Ala Asn Val Lys Ser Gly Ala Ile Met Ser Ala Leu Ser Asp
            20                  25                  30

<210> SEQ ID NO 90
<211> LENGTH: 30
<212> TYPE: PRT
<213> ORGANISM: Rattus rattus

<400> SEQUENCE: 90

Trp Leu Glu Leu Trp Gly Met Pro Ala Trp Tyr Val Ala Ala Cys Arg
1               5                   10                  15

Ala Asn Val Lys Ser Gly Ala Ile Met Ser Ala Leu Ser Asp
            20                  25                  30

<210> SEQ ID NO 91
<211> LENGTH: 30
<212> TYPE: PRT
<213> ORGANISM: Rattus rattus

<400> SEQUENCE: 91

Trp Leu Glu Leu Trp Gly Met Pro Ala Trp Tyr Val Ala Ala Cys Arg
1               5                   10                  15

Ala Asn Val Lys Ser Gly Ala Ile Met Ser Ala Leu Ser Asp
            20                  25                  30

<210> SEQ ID NO 92
<211> LENGTH: 30
<212> TYPE: PRT
<213> ORGANISM: Rattus rattus

<400> SEQUENCE: 92

Trp Leu Glu Leu Trp Gly Met Pro Ala Trp Tyr Val Ala Ala Cys Arg
1               5                   10                  15

Ala Asn Val Lys Ser Gly Ala Ile Met Ala Asn Leu Ser Asp
            20                  25                  30

<210> SEQ ID NO 93
<211> LENGTH: 30
<212> TYPE: PRT
<213> ORGANISM: Rattus rattus

<400> SEQUENCE: 93

Trp Leu Glu Leu Trp Gly Met Pro Ala Trp Tyr Val Ala Ala Cys Arg
1               5                   10                  15

Ala Asn Val Lys Ser Gly Ala Ile Met Ser Ala Leu Ser Asp
            20                  25                  30

<210> SEQ ID NO 94
<211> LENGTH: 35

```
<212> TYPE: PRT
<213> ORGANISM: Homo sapiens

<400> SEQUENCE: 94

Gly Arg Lys Lys Arg Arg Gln Arg Arg Cys Asp Leu Ala Asp Asn
1               5                   10                  15

Ile Glu Arg Leu Lys Ala Asn Asp Gly Leu Lys Phe Ser Gln Glu Tyr
            20                  25                  30

Glu Ser Ile
        35

<210> SEQ ID NO 95
<211> LENGTH: 35
<212> TYPE: PRT
<213> ORGANISM: Homo sapiens

<400> SEQUENCE: 95

Gly Arg Lys Lys Arg Arg Gln Arg Arg Cys Glu Leu Ala Asp His
1               5                   10                  15

Ile Glu Arg Leu Lys Ala Asn Asp Asn Leu Lys Phe Ser Gln Glu Tyr
            20                  25                  30

Glu Ser Ile
        35

<210> SEQ ID NO 96
<211> LENGTH: 35
<212> TYPE: PRT
<213> ORGANISM: Homo sapiens

<400> SEQUENCE: 96

Gly Arg Lys Lys Arg Arg Gln Arg Arg Cys Ile Arg Glu Asp Asp
1               5                   10                  15

Ser Leu Met Leu Tyr Ala Leu Ala Gln Glu Lys Lys Glu Ser Asn Met
            20                  25                  30

His Glu Ser
        35
```